United States Patent
Tegels

(10) Patent No.: US 9,220,489 B2
(45) Date of Patent: Dec. 29, 2015

(54) CLUTCH RELEASE MECHANISM FOR VASCULAR CLOSURE DEVICE

(75) Inventor: Zachary J. Tegels, Minneapolis, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 101 days.

(21) Appl. No.: 13/697,505

(22) PCT Filed: Aug. 18, 2011

(86) PCT No.: PCT/US2011/001451
§ 371 (c)(1),
(2), (4) Date: Nov. 12, 2012

(87) PCT Pub. No.: WO2012/023983
PCT Pub. Date: Feb. 23, 2012

(65) Prior Publication Data
US 2013/0072967 A1    Mar. 21, 2013

Related U.S. Application Data

(60) Provisional application No. 61/375,361, filed on Aug. 20, 2010.

(51) Int. Cl.
*A61B 17/00* (2006.01)
*A61B 17/04* (2006.01)

(52) U.S. Cl.
CPC ......... *A61B 17/0057* (2013.01); *A61B 17/0482* (2013.01); *A61B 17/0483* (2013.01);
(Continued)

(58) Field of Classification Search
CPC ................ A61B 17/0057; A61B 2017/00601; A61B 2017/00615; A61B 2017/00623; A61B 2017/00628; A61B 2017/0065; A61B 2017/00654; A61B 2017/00778; A61B 2017/0417; A61B 2017/0496; A61B 17/0482; A61B 17/0483; A61B 2017/0404; A61B 2017/0414; A61B 2017/0475; A61B 2017/00659
USPC ......... 606/139, 144, 145, 146, 148, 213, 232; 623/23.72
See application file for complete search history.

(56) References Cited

U.S. PATENT DOCUMENTS

| 6,045,569 A | 4/2000 | Kensey et al. |
| 6,056,768 A | 5/2000 | Cates et al. |

(Continued)

FOREIGN PATENT DOCUMENTS

| EP | 1440661 A1 | 7/2004 |
| JP | 2009502419 A | 1/2009 |
| WO | 2006037039 A2 | 4/2006 |

OTHER PUBLICATIONS

PCT International Search Report for International Application No. PCT/US2011/001451, mailed Jan. 17, 2012.

*Primary Examiner* — Ryan Severson
*Assistant Examiner* — Christian Knauss
(74) *Attorney, Agent, or Firm* — Holland & Hart

(57) ABSTRACT

A method and apparatus for sealing a puncture or incision formed percutaneously in a tissue. The apparatus including an anchor, a sealing plug, a filament secured to the sealing plug and the anchor, a compaction member assembly, a spool, a driving plate, and a follower. The compaction member assembly is disposed adjacent the sealing plug and structured and arranged to apply an axially directed compressive force to automatically compact the sealing plug toward the anchor. The spool has a portion of the filament wound thereon. The driving plate is connected to the spool and arranged to contact and apply a force to a proximal end of the compaction member assembly upon rotation of the driving plate to advance the compaction member assembly. The follower is operable between the spool and driving plate to releasably connect the spool and driving plate to provide a clutch action.

23 Claims, 15 Drawing Sheets

(52) U.S. Cl.
CPC ............... *A61B2017/00623* (2013.01); *A61B 2017/00654* (2013.01); *A61B 2017/00659* (2013.01); *A61B 2017/00778* (2013.01); *A61B 2017/0404* (2013.01); *A61B 2017/0414* (2013.01); *A61B 2017/0417* (2013.01); *A61B 2017/0475* (2013.01); *A61B 2017/0496* (2013.01)

(56) References Cited

U.S. PATENT DOCUMENTS

| | | | |
|---|---|---|---|
| 6,090,130 | A | 7/2000 | Nash et al. |
| 7,618,436 | B2 * | 11/2009 | Forsberg ............... 606/213 |
| 7,618,438 | B2 * | 11/2009 | White et al. ............ 606/232 |
| 2003/0204193 | A1 * | 10/2003 | Gabriel et al. .......... 606/139 |
| 2004/0267308 | A1 | 12/2004 | Bagaoisan et al. |
| 2005/0085851 | A1 * | 4/2005 | Fiehler et al. .......... 606/213 |
| 2005/0096696 | A1 * | 5/2005 | Forsberg ............... 606/213 |
| 2005/0096697 | A1 * | 5/2005 | Forsberg et al. ........ 606/213 |
| 2005/0107827 | A1 * | 5/2005 | Paprocki ............... 606/228 |
| 2006/0229672 | A1 * | 10/2006 | Forsberg ............... 606/232 |
| 2006/0229673 | A1 * | 10/2006 | Forsberg ............... 606/232 |
| 2006/0229674 | A1 * | 10/2006 | Forsberg ............... 606/232 |
| 2006/0265006 | A1 * | 11/2006 | White et al. ............ 606/232 |
| 2006/0265007 | A1 * | 11/2006 | White et al. ............ 606/232 |
| 2007/0032823 | A1 * | 2/2007 | Tegg ............. A61B 17/0057 606/232 |
| 2007/0032824 | A1 * | 2/2007 | Terwey ................. 606/232 |
| 2007/0255314 | A1 * | 11/2007 | Forsberg ............... 606/213 |
| 2008/0071311 | A1 * | 3/2008 | White et al. ............ 606/232 |
| 2011/0015670 | A1 * | 1/2011 | Cates et al. ............ 606/213 |
| 2012/0010634 | A1 * | 1/2012 | Crabb et al. ........... 606/144 |
| 2012/0089177 | A1 * | 4/2012 | Tegels ................. 606/213 |

* cited by examiner

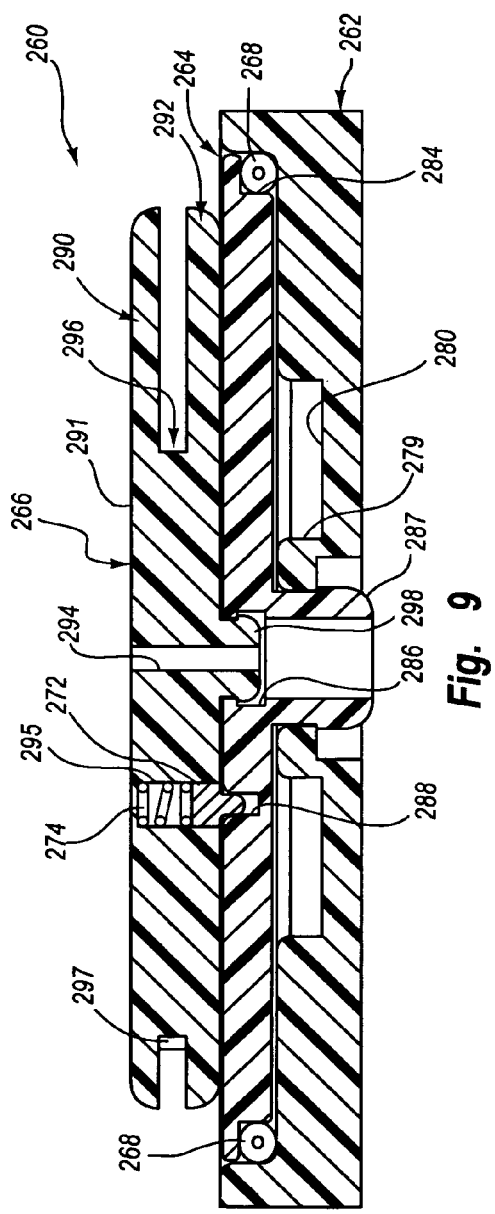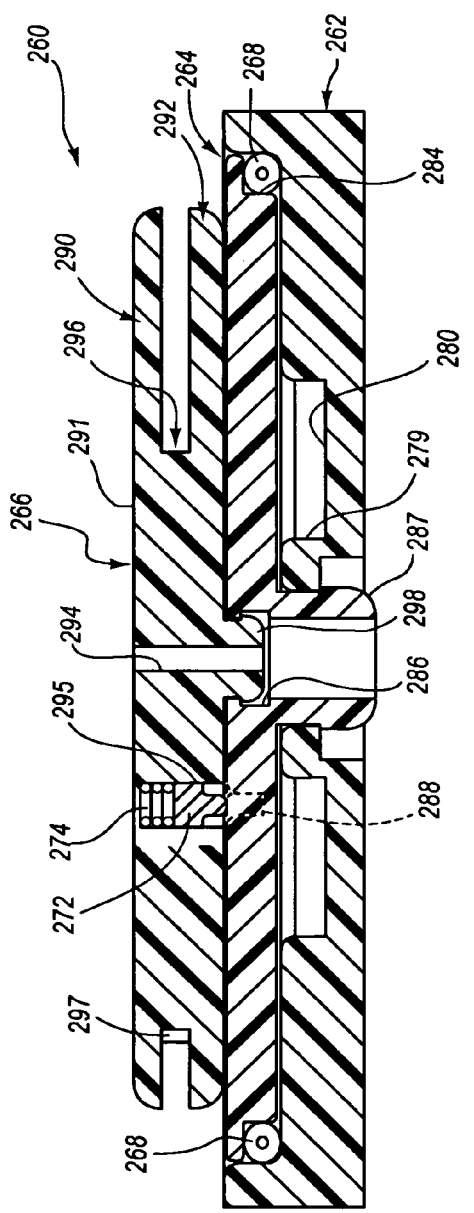

CLUTCH RELEASE MECHANISM FOR VASCULAR CLOSURE DEVICE

RELATED APPLICATION

This claims the benefit of U.S. Provisional Application No. 61/375,361, filed 20 Aug. 2010, which is hereby incorporated by reference herein in its entirety.

TECHNICAL FIELD

The present disclosure relates generally to medical devices and more particularly to devices for sealing punctures or incisions in a tissue wall.

BACKGROUND

Various surgical procedures are routinely carried out intravascularly or intraluminally. For example, in the treatment of vascular disease, such as arteriosclerosis, it is a common practice to invade the vessel and insert an instrument (e.g., a balloon or other type of catheter) to carry out a procedure within the vessel. Such procedures usually involve the percutaneous puncture of the vessel so that an insertion sheath may be placed in the vessel and thereafter instruments (e.g., catheters) may pass through the sheath to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices, such as those described in U.S. Pat. Nos. 6,090,130 and 6,045,569, which are hereby incorporated herein in their entireties by this reference.

Typical closure devices such as the ones described in the above-mentioned patents place a sealing plug at the tissue puncture site. Successful deployment of the sealing plug, however, requires that it be manually ejected from within a device sheath and compacted down to an outer surface of the tissue puncture using a compaction tube. The compaction procedure cannot commence until the device sheath (within which the compaction tube is located) has been removed so as to expose the compaction tube for manual grasping. Under certain conditions, removal of the sheath prior to compacting the sealing plug may cause the sealing plug itself to be displaced proximally from the tissue puncture, hindering subsequent placement of the sealing plug, and resulting in only a partial seal and associated late bleeding from the tissue puncture. Accordingly, there is a need for improving the mechanism for deployment of the sealing plug at the site of a tissue puncture.

SUMMARY

The present disclosure meets the above-described needs and others. Specifically, the present disclosure provides methods and systems for closing internal tissue punctures. However, unlike prior systems, the present disclosure provides automatic compaction to a sealing plug as the closure device is retracted. In addition, the present disclosure allows the automatic compaction system to disengage, facilitating full retraction of the closure device and easy separation of the sealing plug from the remainder of the closure device.

In one of many possible embodiments, the present disclosure provides a tissue puncture closure device that includes an anchor, a sealing plug, a filament, a compaction member, a spool, a driving plate, and a follower. The filament is secured between the sealing plug and the anchor. The compaction member assembly is disposed adjacent to the sealing plug and structured and arranged to apply an axially directed compressive force to automatically compact the sealing plug toward the anchor. The compaction member assembly has a distal end and a proximal end. The spool has a portion of the filament wound thereon. The driving plate is connected to the spool and arranged to contact and apply a force to the proximal end of the compaction member assembly upon rotation of the driving plate to advance the compaction member assembly. The follower is operable between the spool and driving plate to releasably connect the spool and driving plate.

The compaction member assembly may further include a compaction tube and a coil, wherein the coil is structured and arranged to apply an axially directed compressive force to the compaction tube to drive the compaction tube to automatically compact the sealing plug toward the anchor. The spool may include a cam portion with a portion of the filament being wrapped around the cam portion, wherein unwinding the filament from the spool applies a variable rotation force to the driving plate. The spool may include first and second outer plates and a cam portion positioned between the first and second outer plates. The cam portion may define a cam surface having a variable radius, wherein a portion of the filament wraps around the cam portion.

The follower may be mounted to the spool and biased toward the driving plate. The driving plate may include at least one recess sized to receive a portion of the follower. The compaction member assembly may include a compaction tube and a coil member arranged end-to-end. The compaction tube may define the distal end of the compaction member assembly and the coil defines the proximal end of the compact member assembly. The driving plate includes a coil track defined in a peripheral surface of the driving plate, and a portion of the compaction member assembly may be positioned in the coil track.

Another aspect of the present disclosure relates to a tissue puncture closure device for partial insertion into and sealing of a tissue puncture in an internal tissue wall accessible through a percutaneous incision. The device includes an anchor, a sealing plug, a filament, a compaction member, a storage spool, a driving plate, and at least one follower. The anchor is disposed on a distal side of the internal tissue wall. The sealing plug is disposed on a proximal side of the internal tissue wall. The filament is connected to and anchored at a distal end to the anchor and sealing plug, and is slidable and cinchable along the filament toward the anchor to close the tissue puncture. The compaction member assembly is disposed on the filament and arranged to drive the sealing plug along the filament distally towards the anchor. The storage spool has a proximal end of the filament wound thereon. The driving plate is connected to the storage spool and configured to contact a proximal end of the compaction member assembly to advance the compaction member assembly. The at least one follower is mounted to the storage spool and biased into contact with the driving plate to releasably resist relative rotational movement between the storage spool and driving plate.

The driving plate may include at least one recess configured to receive a portion of the at least one follower. The at least one recess may include a plurality of recesses arranged in a circle. The at least one follower may move out of the at least one recess when a threshold torsional force applied to the storage spool by the filament is exceeded. The storage spool may include a cam portion about which the proximal end of the filament is wound. The storage spool is configured to apply a variable rotational force to the driving plate when the filament unwinds from the cam portion.

A further aspect of the present disclosure is directed to a method of sealing a tissue puncture in an internal tissue wall of a vessel that is accessible through a percutaneous incision. The method includes providing a closure device having an anchor, a sealing plug, a filament secured between the sealing plug and the anchor, a compaction member assembly, a spool having a portion of the filament wound thereon, a driving plate, and at least one follower arranged to resist relative rotational movement between the driving plate and spool. A distal end of the compaction member assembly is disposed adjacent the sealing plug, a proximal end of the compaction member assembly is in contact with the driving plate, and the driving plate is connected to the spool. The method also includes inserting the anchor through the tissue puncture, withdrawing the closure device from the tissue puncture with the anchor positioned within the vessel, wherein withdrawing the closure device rotates the spool, and rotating the spool rotates the driving plate to drive the compaction member assembly and compact the sealing plug toward the anchor. In the method, further withdrawing the closure device until the at least one follower disconnects from at least one of the spool and driving plate permits relative rotation between the spool and driving plate.

The at least one follower may be mounted to the spool and biased into contact with the driving plate with a biasing member. The at least one follower may include a plurality of followers biased into contact with the driving plate.

Another aspect of the present disclosure relates to a method of sealing a tissue puncture in an internal tissue wall accessible through a percutaneous incision. The method includes providing a tissue puncture closure device comprising an anchor, a sealing plug, a filament, a compaction member assembly, a driving plate, a spool having a cam member, and at least one follower, the filament being connected at its distal end to the anchor, to the sealing plug located proximal of the anchor, and to the cam member of the spool at its proximal end. The at least one follower is operable to releasably connect the spool and driving plate. The method also includes inserting the tissue puncture closure device into the percutaneous incision, deploying the anchor into the tissue puncture, and automatically compacting the sealing plug toward the anchor upon withdrawal of the tissue puncture closure device from the internal tissue wall puncture. Automatically compacting includes unwinding the filament from the spool to rotate the spool and driving plate together to apply a variable force to the compaction member assembly to advance a distal end of the compaction member assembly. The method further includes operating the at least one follower to release the spool from rotating with the driving plate, and cutting the filament to leave the anchor and sealing plug at the tissue puncture.

The step of operating the at least one follower may include applying a withdrawal force to the tissue puncture closure device to exceed a threshold torsional force applied to the spool by unwinding in the filament to automatically move the at least one follower relative to at least one of the spool and driving plate. The driving plate may include a plurality of follower recesses arranged to receive the at least one follower at different relative rotated positions between the driving plate and spool. The tissue puncture closure device may include a housing and a base upon which the driving plate and spool are mounted, wherein the base is movable within the housing to permit ejection of the sealing plug from the tissue puncture closure device without compacting the sealing plug.

Additional advantages and novel features will be set forth in the description which follows or can be learned by those skilled in the art through reading these materials or practicing the examples disclosed herein.

BRIEF DESCRIPTION OF THE DRAWINGS

The accompanying drawings illustrate various embodiments of the present disclosure and are a part of the specification. The illustrated embodiments are merely examples and do not limit the scope of the invention.

FIG. 9 is a cross-sectional view of the automatic driving assembly of FIG. 7 taken along cross-section indicators 9-9 with a spool assembly and driving plate connected together.

FIG. 10 is a cross-sectional view of the automatic driving assembly of FIG. 9 with the spool assembly and driving plate disconnected to permit relative rotation therebetween.

Throughout the drawings, identical reference numbers designate similar, but not necessarily identical, elements.

DETAILED DESCRIPTION

Figure 1:
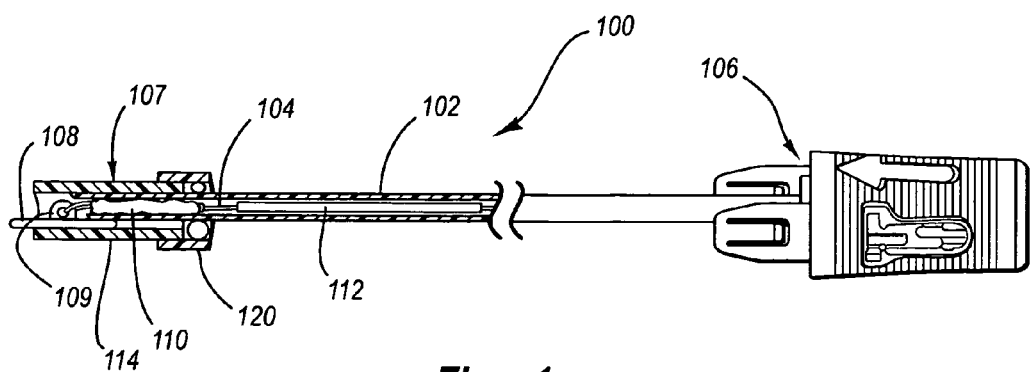
FIG. 1 is a partial cut-away view of a tissue puncture closure device according to the prior art.

As mentioned above, vascular procedures are conducted throughout the world and require access to a vessel through a puncture. Most often, the vessel is a femoral artery. To close the puncture following completion of a procedure, many times a closure device is used to sandwich the puncture between an anchor and a sealing plug. However, sometimes the sealing plug is difficult to eject from the sealing device and may not properly seat against an exterior situs of the arteriotomy. If the plug does not seat properly against the arteriotomy, there is a potential for elongated bleeding.

The present disclosure describes methods and apparatuses that facilitate sealing plug ejection and proper placement of the sealing plug. One aspect of the present disclosure is directed to the use of a cam structure in a vascular closure device as part of an automatic or semi-automatic driving assembly. The cam structure may contact or be coupled to a compaction member assembly that is used to compact the sealing plug. The compaction member assembly may include a compaction tube that is arranged to contact the sealing plug. The compaction member assembly may also include a compaction tube driver (e.g., a coiled structure) positioned between the compaction tube and the cam structure. The cam structure may include at least one cam surface, and rotation of the cam structure contacts the cam surface with compaction tube driver to advance the compaction tube. The cam member may be coupled to a spool about which a portion of a suture is wound, wherein the suture is used to connect the sealing plug and an anchor of the vascular closure device together. The cam member may apply a variable driving force to the proximal end of the compaction assembly upon rotation of the spool. In some arrangements, the cam member is constructed as a driving plate that is arranged coaxially with the spool and is rotated upon rotation of the spool. The cam member may have a generally thin, flat construction. The cam member interface with the compaction assembly by, for example, contacting a proximal end of the compaction assembly, or may interface with an interference fit, clamp, or other type of interface at a location distal of a proximal end of the compaction assembly. A clutch may be to operable between the driving plate and spool.

While the vascular instruments shown and described below include procedure sheaths and puncture sealing devices, the application of principles described herein are not limited to the specific devices shown. The principles described herein may be used with any medical device. Therefore, while the description below is directed primarily to arterial procedures and certain embodiments of a vascular closure device, the methods and apparatus are only limited by the appended claims.

As used in this specification and the appended claims, the terms "compact," "compaction," and "compacting" are used broadly to mean packing down and compressing by one or a succession of blows or taps or smooth, steady pressure, but not by excessive force. The terms "tamp" and "tamping" may relate to certain types or forms of "compaction" and "compacting." "Engage" and "engabable" are also used broadly to mean interlock, mesh, or contact between two devices. Likewise "disengage" or "disengagable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as used in the specification, including the claims, have the same meaning as the word "comprising."

Referring to FIGS. 1-4, a vascular closure device 100 is shown according to the prior art. Some example closure devices are disclosed in U.S. Published Patent Application No. 2005/0085851 and U.S. Pat. Nos. 7,618,438 and 7,618, 436, which references are incorporated herein in their entireties by this reference. The vascular closure device 100 includes a carrier tube 102 with a filament or suture 104 extending at least partially therethrough. The vascular closure device 100 also includes a first or proximal end 106 and a second or distal end 107. External to the distal end 107 of the carrier tube 102 is an anchor 108. The anchor may include an elongated, stiff, low profile member including an eye 109 formed at the middle. The anchor 108 is typically made of a biologically resorbable polymer.

The suture 104 is threaded through the anchor 108 and back to a collagen pad 110. The collagen pad 110 may comprise, for example, randomly oriented fibrous material bound together by chemical means. The collagen pad 110 is slidingly attached to the suture 104 as the suture passes distally through the carrier tube 102. As the suture traverses the anchor 108 and reenters the carrier tube 102, the suture 104 is securely slip-knotted proximal to the collagen pad 110 to facilitate cinching of the collagen pad 110 when the vascular closure device 100 is properly placed and the anchor 108 deployed (see FIG. 4).

The carrier tube 102 typically includes a compaction member 112 disposed therein. The compaction member 112 is slidingly mounted on the suture 104 and may be used by an operator to compact the collagen pad 110 toward the anchor 108 at an appropriate time to seal a percutaneous tissue puncture.

Prior to deployment of the anchor 108 within a vessel (e.g., an artery), the eye 109 of the anchor 108 rests outside the distal end 107 of the carrier tube 102. The anchor 108 may be temporarily held in place flush with the carrier tube 102 using a bypass tube 114 that is disposed over the distal end 107 of the carrier tube 102.

Figure 2:
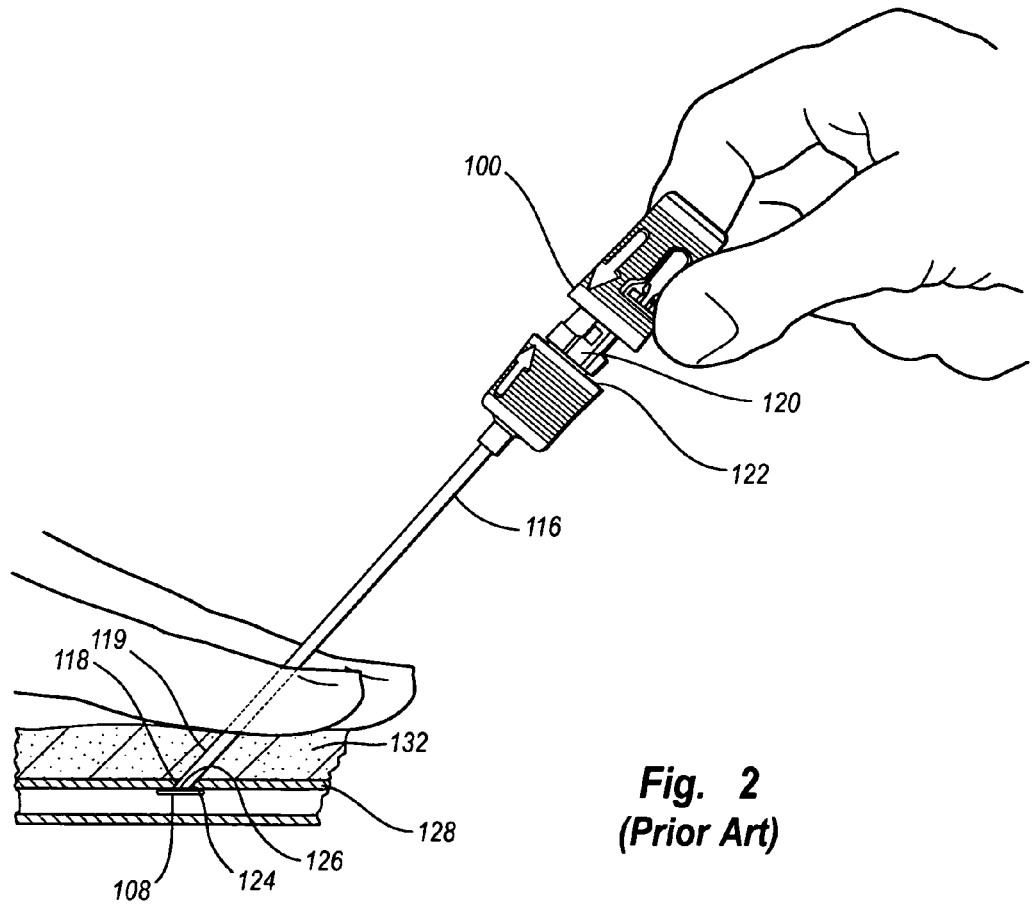
FIG. 2 is a side view of the tissue puncture closure device of FIG. 1 engaged with a vessel according to the prior art.
Figure 3:
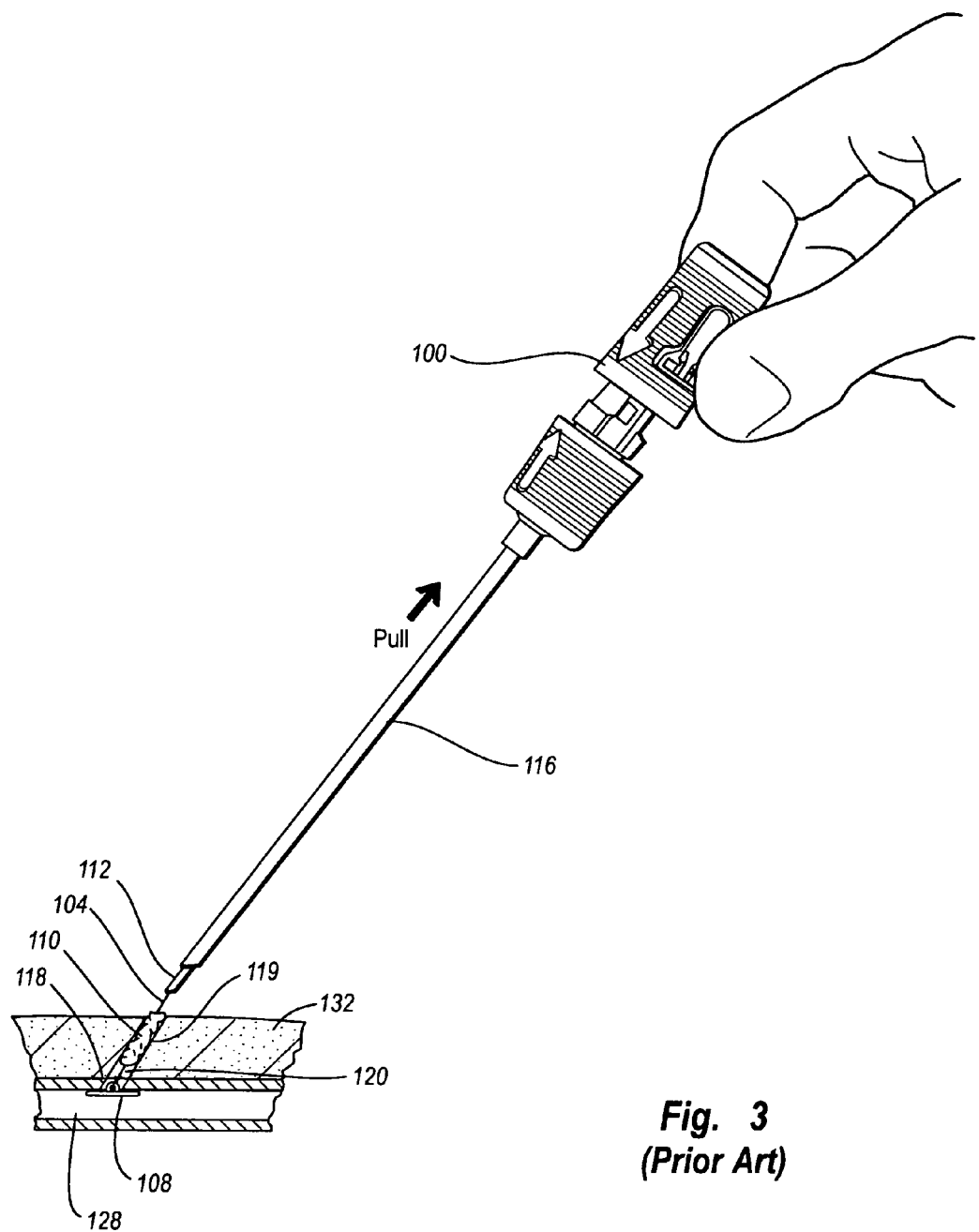
FIG. 3 is a side view of the tissue puncture closure device of FIG. 1 being withdrawn from a vessel according to the prior art to deploy a sealing plug.
Figure 4:
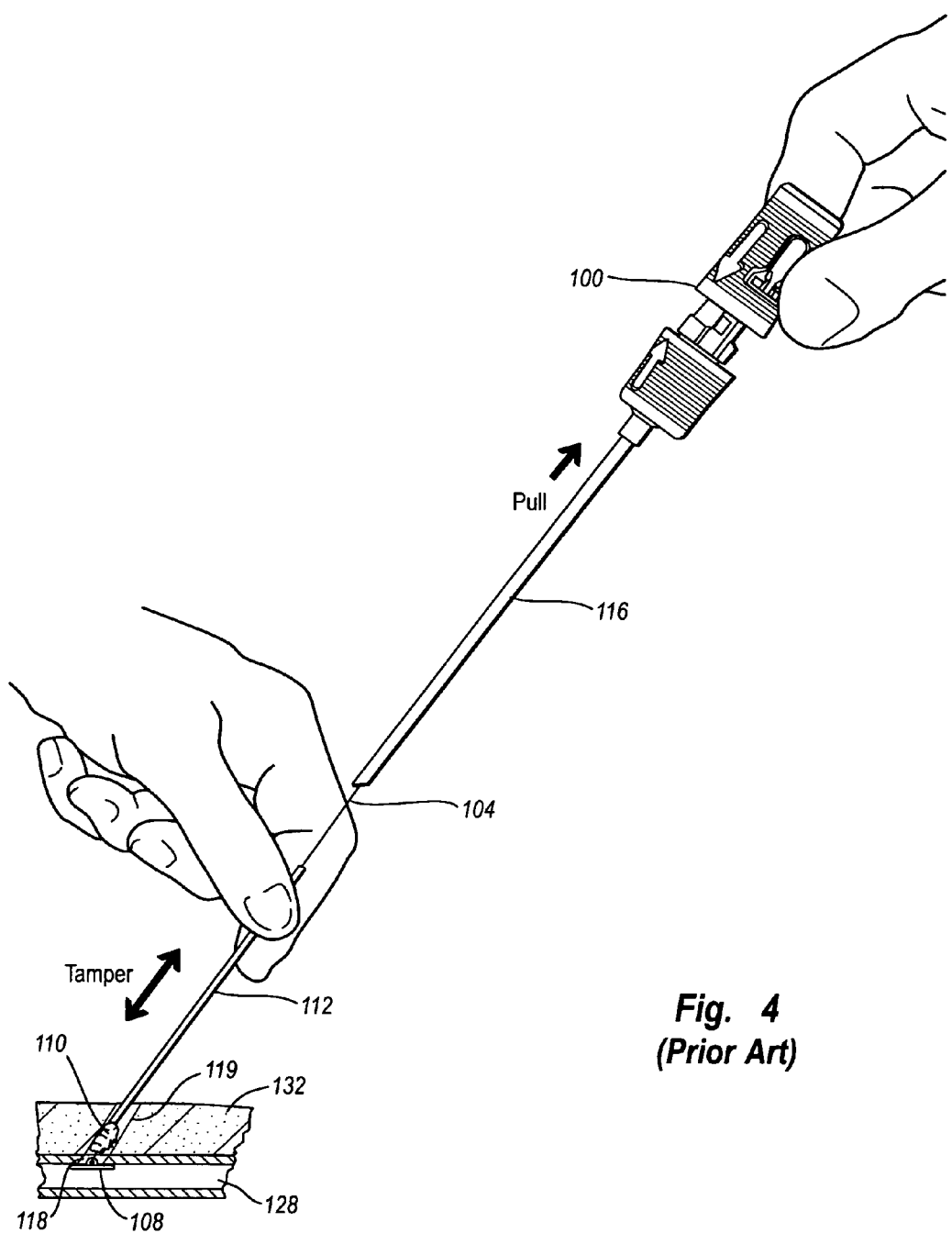
FIG. 4 is a side view of the tissue puncture closure device of FIG. 1 illustrating compaction of the sealing plug according to the prior art.

The flush arrangement of the anchor 108 and carrier tube 102 allows the anchor 108 to be inserted into a sheath such as insertion sheath 116 as shown in FIGS. 2-4, and eventually through a tissue (e.g., arterial) puncture 118. The insertion sheath 116 is shown in FIGS. 2-4 inserted through a percutaneous incision 119 and into a vessel 128. The bypass tube 114 (see FIG. 1) includes an oversized head 120 that prevents the bypass tube 114 from passing through an internal passage of the insertion sheath 116. As the vascular closure device 100 is inserted into the insertion sheath 116, the oversized head 120 bears against a surface 122 of insertion sheath 116.

Further insertion of the vascular closure device 100 results in sliding movement between the carrier tube 102 and the bypass tube 114, thereby releasing the anchor 108 from the bypass tube 114 (see FIG. 1). The anchor 108 typically remains in the flush arrangement shown in FIG. 1 following release from the bypass tube 114, limited in movement by the insertion sheath 116.

The insertion sheath 116 may include a monofold at a second or distal end 126 thereof. The monofold acts as a one-way valve to the anchor 108. A monofold is typically a plastic deformation in a portion of the insertion sheath 116 that elastically flexes as the anchor 108 is pushed out through the distal end 126 of the insertion sheath 116. Typically, after the anchor 108 passes through the distal end 126 of the insertion sheath 116 and enters the vessel 128, the anchor 108 is no longer constrained to the flush arrangement with respect to the carrier tube 102 and it deploys and rotates to the position shown in FIG. 2.

The insertion sheath 116 may include a pair of closure device connection apertures (not shown) and a carrier tube aperture (not shown) at a proximal surface 122 (see FIG. 1). The carrier tube 102 is inserted into the carrier tube aperture and the sheath connection members 130 are inserted into and releasably engage with the closure device connection apertures when assembling the vascular closure device 100 with the insertion sheath 116.

Referring next to FIGS. 3-4, with the anchor 108 deployed, the vascular closure device 100 and the insertion sheath 116 are withdrawn together, ejecting the collagen pad 110 from the carrier tube 102 into the percutaneous incision 119 and exposing the compaction member 112. With the compaction member 112 fully exposed as shown in FIG. 4, the collagen pad 110 is manually compacted, and the anchor 108 and collagen pad 110 are cinched together and held in place with the self-tightening slip-knot on the suture 102. The tissue puncture is sandwiched between the anchor 108 and the collagen pad 110, thereby sealing the tissue puncture 118. The suture 104 is then cut and the percutaneous incision 119 may be closed. The suture 104, anchor 108, and collagen pad 110 are generally made of resorbable materials and therefore remain in place while the tissue puncture 118 heals.

It may be difficult to eject and compact the collagen pad 110 using the typical vascular closure device 100 described above. The insertion sheath 116 resists deformation as the collagen pad 110 is ejected from the carrier tube and compaction does not commence until the insertion sheath 116 has been removed so as to expose the compaction member 112 for manual grasping. Under certain conditions, removal of the insertion sheath 116 prior to compacting the collagen pad 110 causes the collagen pad 110 to retract or displace proximally from the tissue puncture 118, creating an undesirable gap between the collagen pad 110 and the tissue puncture 118.

The general structure and function of tissue puncture closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

Referring now to FIGS. 5A-5H, an apparatus, for example a tissue puncture closure device 200, is shown according to one embodiment of the present disclosure. The closure device 200 is shown in an exploded assembly view in FIGS. 5A-5B. FIGS. 5C-5H illustrate the closure device 200 assembled and inserted through a procedure sheath 216 and into a lumen 232. The closure device 200 has particular utility when used in connection with intravascular procedures, such as angiographic dye injection, cardiac catheterization, balloon angioplasty and other types of recanalizing of atherosclerotic arteries, etc. as the closure device 200 is designed to cause immediate hemostasis of the blood vessel (e.g., arterial) puncture. However, it will be understood that while the description of the preferred embodiments below are directed to the sealing off of percutaneous punctures in arteries, such devices have much more wide-spread applications and may be used for sealing punctures or incisions in other types of tissue walls as well. Thus, the sealing of a percutaneous puncture in a vessel, shown herein, is merely illustrative of one particular use of the closure device 200 according to principles of the present disclosure.

The closure device 200 includes a first or proximal end portion 206 and a second or distal end portion 207. A carrier tube 202 extends from the proximal end portion 206 to the distal end portion 207 and includes an outlet 213 at the distal end portion 207. The distal end portion 207 may include a slit 209.

The carrier tube 202 may be made of plastic or other material and is designed for insertion through the procedure sheath 216. The procedure sheath 216 is designed for insertion through a percutaneous incision 219 in a tissue layer 230 and into the lumen 232. According to FIGS. 5B-5H, the lumen 232 comprises an interior portion of a vessel 228 (e.g., a femoral artery).

At the distal end portion 207 of the carrier tube 202 there is an anchor 208 and a sealing plug 210. The anchor 208 of the present embodiment is an elongated, stiff, low-profile member arranged to be seated inside the vessel 228 against a vessel wall 234 contiguous with a tissue puncture 218. The anchor 208 is preferably made of a biologically resorbable polymer. The sealing plug 210 is formed of a compressible sponge, foam, or fibrous mat made of a non-hemostatic biologically resorbable material such as collagen, and may be configured in any shape so as to facilitate sealing the tissue puncture 218.

Figure 5A:
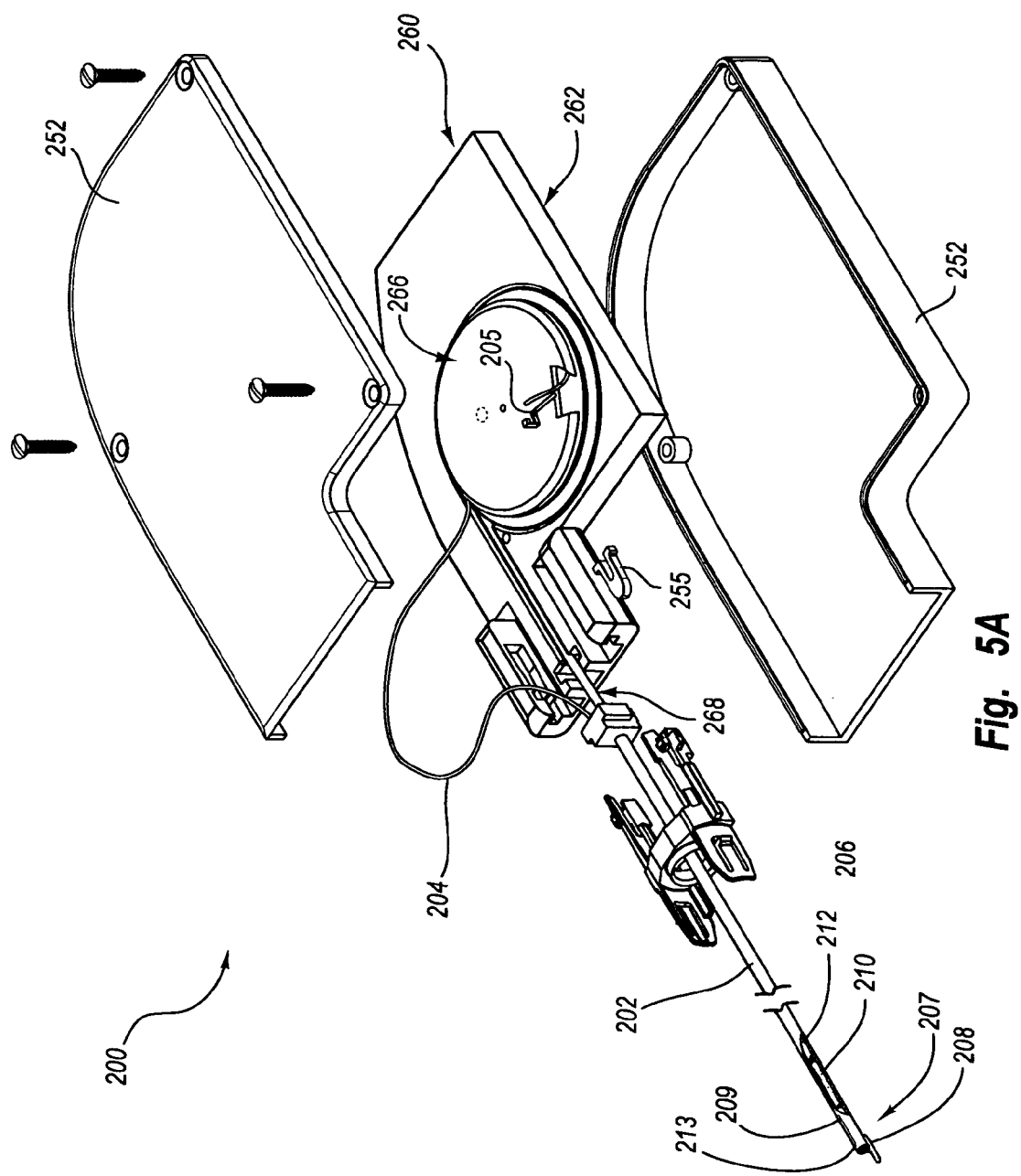
FIG. 5A is an exploded perspective view of an example tissue puncture closure device with an automatic compaction or driving mechanism according to the present disclosure.

The sealing plug 210 and anchor 208 are connected to one another by a connector such as a filament or suture 204 that is also biologically resorbable. The anchor 208, the sealing plug 210, and the suture 204 may be collectively referred to as the "closure elements" below. As shown in FIG. 5A, the anchor 208 is initially arranged adjacent to and exterior of the distal end portion 207 of the carrier tube 202, while the sealing plug 210 is initially disposed within the carrier tube 202. The anchor 208 is shown nested in its low profile configuration along the carrier tube 202 to facilitate insertion into the lumen 232 in FIGS. 5A-5B, and deployed abutting the vessel wall 234 in FIGS. 5C-5H.

The suture 204 extends distally from the proximal end portion 206 of the closure device 200 through the carrier tube 202. The suture 204 may be threaded through one or more perforations in the sealing plug 210, through a hole in the anchor 208, and proximally back toward the carrier tube 202 to the sealing plug 210. The suture 204 is preferably threaded again through a perforation or series of perforations in the sealing plug 210. The suture 204 may also be threaded around itself to form a self-tightening slip-knot. The suture 204 may thus connect the anchor 208 and the sealing plug 210 in a pulley-like arrangement to cinch the anchor 208 and the sealing plug 210 together when the carrier tube 202 is pulled away from the anchor 208 and the sealing plug 210. The anchor 208 and the sealing plug 210 sandwich and lock together with the suture 204, sealing the tissue puncture 218.

The carrier tube 202 may house a compaction device or compaction member, such as a compaction tube 212, for advancing the sealing plug 210 along the suture 204 and toward the anchor 208. The compaction tube 212 is shown located partially within the carrier tube 202 and proximal of the sealing plug 210. The compaction tube 212, however, may also extend through a handle or housing 252 of the closure device 200. The compaction tube 212 is preferably an elongated tubular or semi-tubular member that may be rigid or flexible and formed of any suitable material. For example, according to one embodiment, the compaction tube 212 is made of polyurethane. The suture 204 extends through at least a portion of the compaction tube 212. For example, as shown in FIGS. 5A-5H, the suture 204 extends along the compaction tube 212 between the proximal and distal end portions 206, 207. However, the suture 204 is not directly connected to the compaction tube 212. Accordingly, the suture 204 and the compaction tube 212 may slide past one another.

According to the embodiment of FIGS. 5A-5H, the suture 204 attaches to an automatic driving assembly 260. The automatic driving assembly 260 may include a base 262, a driving plate 264, a spool assembly 266, a coil 268, a release member 270, and a clutch assembly that includes a follower 272 and a follower biasing member 274. The automatic driving assembly 260 may, in some arrangements, also include the compaction tube 212 and carrier tube 202. In other arrangements, features of the automatic driving assembly 260, such as the coil 268, may be eliminated or provided as a separate feature of the tissue puncture closure device 200.

The base 262 may include a distal end 275, a connector recess 276, a coil recess 278, a mounting hub 279, a spool recess 280, and first and second release member apertures 281, 282. The base 262 is movable within the housing 252. As shown in FIG. 5E, the base 262 may slide forward in the housing 252 until the distal end 275 contacts a stop, such as an internal surface of the housing 252.

The connector recess 276 may be sized to receive a connector feature used to secure the carrier tube 202 to the automatic driving assembly 260. The coil recess 278 may be sized to receive a portion of the coil 268. The spool recess 280 may be sized to receive at least portions of the driving plate 264, spool assembly 266, release member 270, and other features of the automatic driving assembly 260. The first and second release member apertures 281, 282 may be sized and arranged to receive portions of the release member 270, such as a contact portion 271 that rotates into and out of the spool recess 280 for contact with a portion of the driving plate 264. The mounting hub 279 may be arranged to support the driving plate 264 and spool assembly 266 within the spool recess 280.

Figure 5B:
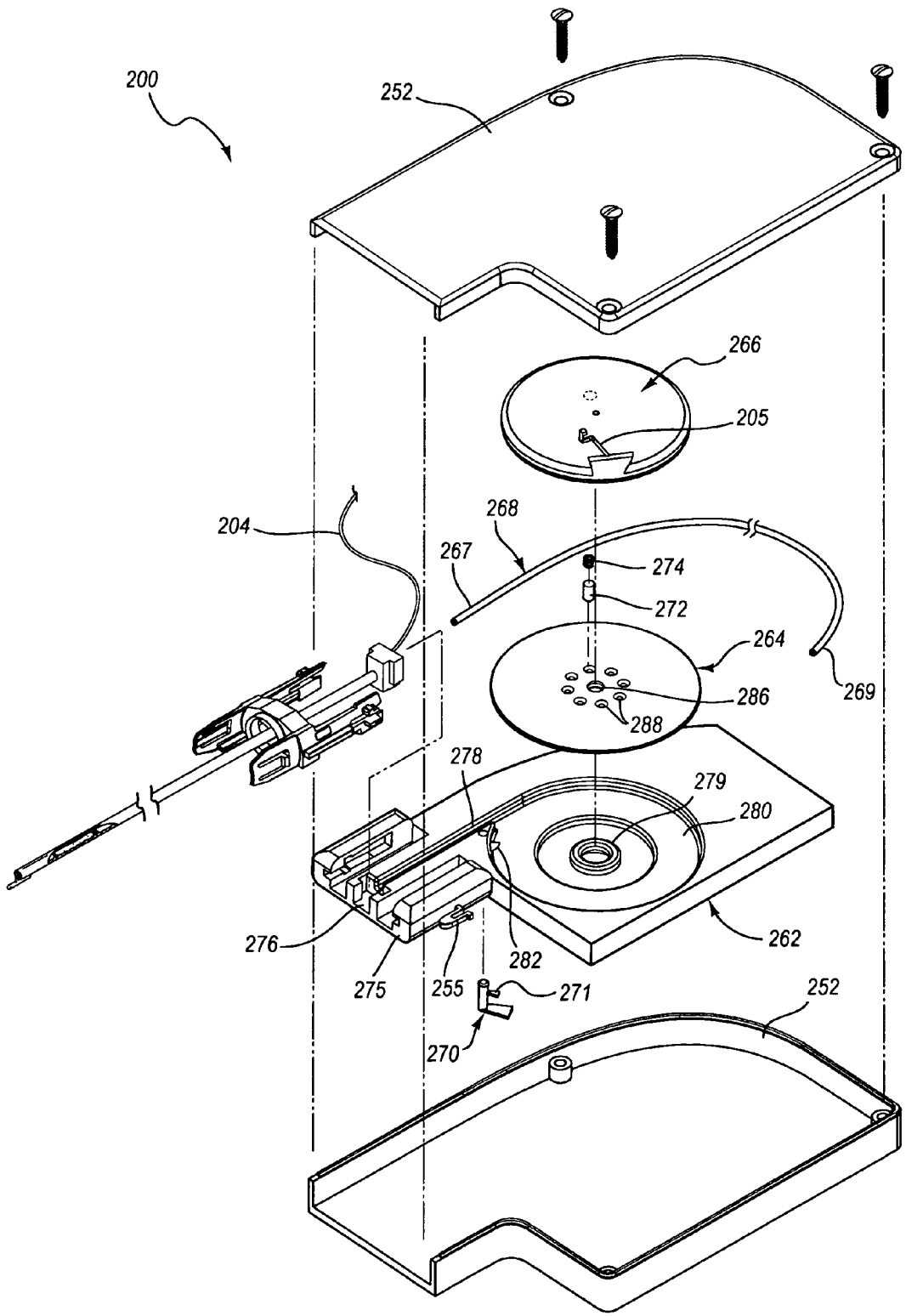
FIG. 5B is another exploded perspective view of the tissue puncture closure device of FIG. 5A.

The driving plate 264 may include a coil track 284, a coil stop 285, a connector aperture 286, a plate connector 287, and a plurality of follower recesses 288 (see FIGS. 5B, 9 and 10). The coil track 284 may be sized to receive a portion of the coil 268. The coil track 284 may be defined around a periphery of the driving plate 264. In one arrangement, the coil track 284 extends around an entire periphery of the driving plate 264. In other arrangements, the coil track 284 may be defined by other portions of the driving plate 264 such as, for example as a recess in a top or bottom surface of the driving plate 264, or a recess or track defined in a surface of the base 262 or spool assembly 266.

The coil stop 285 may be positioned in the coil track 284. The coil stop 285 may define a contact surface against which a portion of the compaction tube assembly (e.g., a proximal end of the coil 268) contacts to transfer rotational forces from the driving plate 264 to longitudinal movement of the compaction tube assembly. Typically, rotation of the driving plate 264 advances the compaction tube assembly by applying a force to a proximal end of the compaction tube assembly (e.g., a proximal end of the coil 268 or the compaction tube 212). In other arrangements, other features of the driving plate 264, such as a compression fit between the coil 268 and coil track 284, may be used to transfer the rotational forces of the driving plate 264 to advance the compaction tube assembly.

The connector aperture 286 may be sized to receive a connection feature of the spool assembly 266. An interface defined between the driving plate 264 and spool assembly 266 at least in part by the connector aperture 286 may provide alignment and connection between the driving plate 264 and spool assembly 266.

The plate connector 287 may be used to connect the driving plate 264 to the base 262. In one example, the plate connector 287 is insertable into the mounting hub 279 to provide a connection between the driving plate 264 and base 262. The plate connector 287 may be releasably or permanently connected to the base 262 via the plate connector 287.

The driving plate 264 may include at least one follower recess 288 sized and arranged to receive the follower 272. The follower 272 may be carried by the spool assembly 266 and biased toward the driving plate 264 by the biasing member 274. The follower 272 may be configured to stay positioned in the follower recess 288 until a threshold torsional force is applied by unwinding the suture 204 from the spool assembly 266. The suture 204 unwinds from the spool assembly 266 by retracting the housing 252 when the anchor 208 is retained within the vessel 228 as will be described in more detail below.

The follower recess 288 and follower 272 may be reversed in other embodiments so that the follower recess 288 is defined in the spool assembly 266 and the follower 272 is carried by the driving plate 264. The follower recesses 288 may be arranged in a circular pattern (see FIG. 5B) around the connector aperture 286. The follower 272 may move into and out of the follower recesses 288 as the driving plate 264 and spool assembly 266 rotate relative to each other.

The follower recesses 288 may have different sizes and shapes that provide differences in the amount of tortional force applied by the spool assembly 266 that is required to move the follower 272 out of the follower recesses 288. The follower recesses 288 may have a circular cross-sectional shape. The follower recesses 288 may have a cross-sectional shape that matches a cross-sectional shape of the follower 272. The follower recesses 288 may have a cross-sectional shape that changes along its length. The follower recesses 288 may be tapered. Typically, the follower recesses 288 have a depth that is less than a total length of the follower 272 so that the follower 272, when positioned in the follower recesses 288, also remains at least partially positioned in the spool assembly 266.

The spool assembly 266 may include a top plate 290 defining a top surface 291, a bottom plate 292 defining a bottom surface 293, a central aperture 294, a follower cavity 295 offset from the central aperture 294, a cam member 296, and a spool connector 298. The cam member 296 defines a cam surface 297. The top and bottom plates 290, 292 and cam member 296 may be defined as separate pieces that are connected together as an assembly. Alternatively, the top and bottom plates 290, 292 and cam member 296 may be integrally formed as a single piece. The cam surface 297 may be accessible around a periphery of the spool assembly 266 for wrapping of the suture 204. A proximal end of the suture 204 may be secured to the spool assembly 266 at a suture connector 205 (see FIG. 5B).

Figure 12:
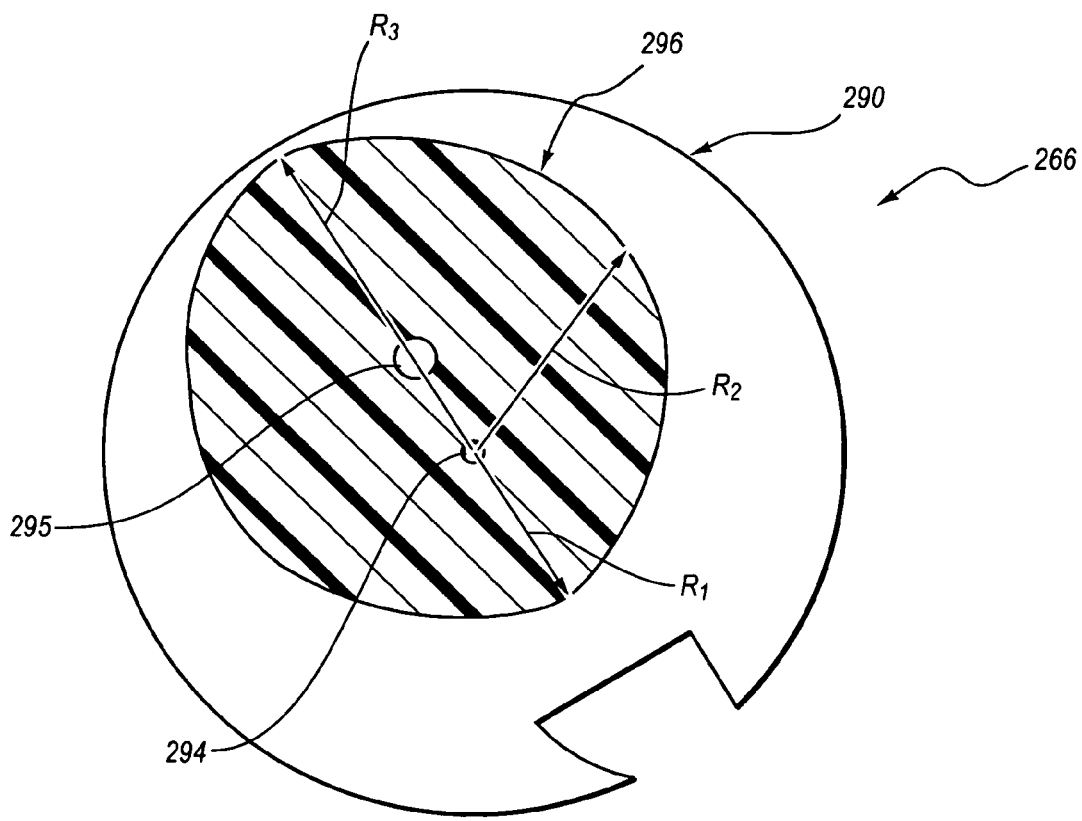
FIG. 12 is a cross-sectional view of the spool assembly of FIG. 11 taken along cross-section indicators 12-12.

FIG. 12 illustrates an example construction for the cam member 296. The cam member 296 may have a variable radius measured from the central aperture 294 (about which the spool assembly 266 rotates) to the cam surface 297. The radius may change from a smallest size $R_1$ to larger sizes $R_2$ and $R_3$ as the suture wraps along the cam surface 297. Unwinding the suture 204 from the spool assembly 266 provides a variable torsional force due to the variable radius $R_1$-$R_3$ of the cam member 296. Many other shapes and sizes are possible for the cam member 296. In some arrangements, the cam surface 297, about which the suture 204 is wound, is defined at least in part by, for example, one or more of the top and bottom plates 290, 292, or a peripheral surface of the spool assembly 266, which may be defined by some other feature.

The spool connector 298 may be sized to extend into the connector aperture 286 of the driving plate 264 (see FIGS. 9 and 10). In some arrangements, the spool assembly 266 may be connected to the driving plate 264 by an interface fit or a snap-fit connection between the spool connector 298 and the connector aperture 286. In other arrangements, the spool connector 298 and connector aperture 286 may be reversed so that the spool connector 298 extends from the driving plate 264 and into the connector aperture 286 defined in the spool assembly 266.

The release member 270 may include a contact portion 271 (see FIG. 5B). The contact portion 2 may move into and out of the spool recess 280 through the second release member aperture 282 upon rotation of the release member 270 to make contact with the driving plate 264. When contacting the driving plate 264, the release member 270 may limit rotation of the driving plate 264 relative to the base 262. When out of contact with the driving plate 264, the release member 270 no longer limits rotation of the driving plate 264 so the driving plate 264 and spool assembly 266 may rotate to permit unwinding of the suture 204.

Figure 6A:
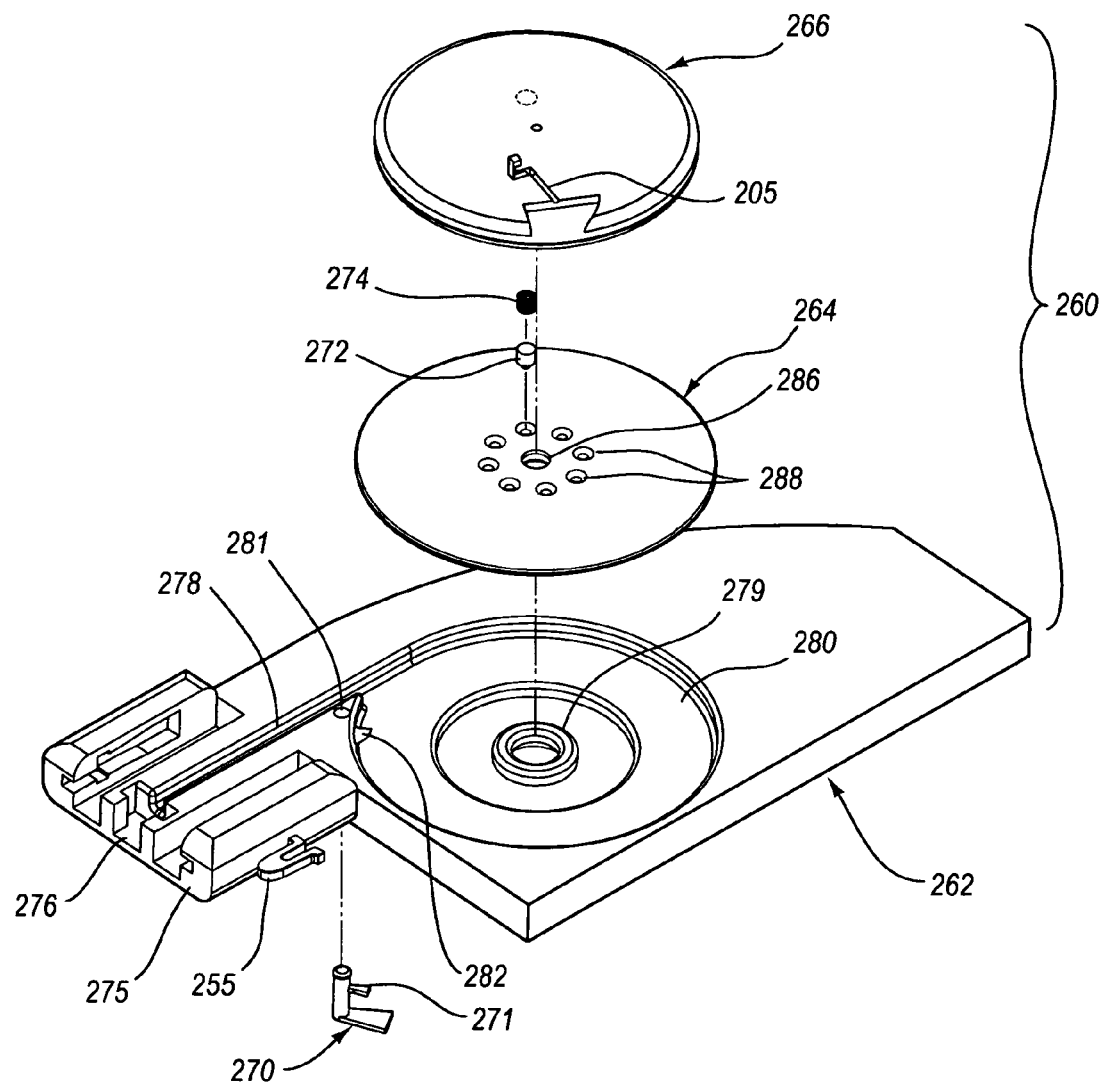
FIG. 6A is a top exploded perspective view of the automatic driving assembly of FIG. 5A.
Figure 6B:
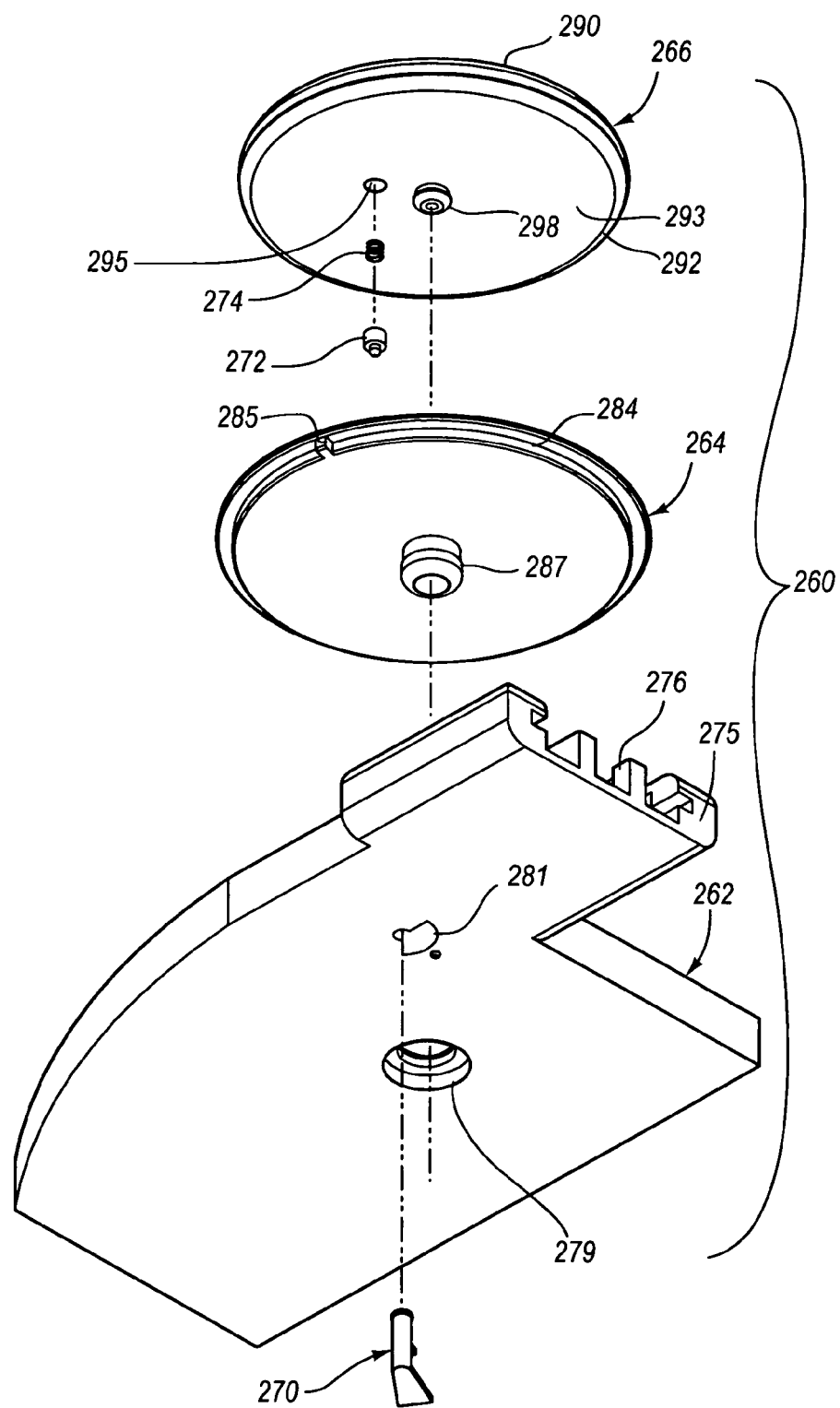
FIG. 6B is a bottom exploded perspective view of the automatic driving assembly of FIG. 5A.
Figure 7:
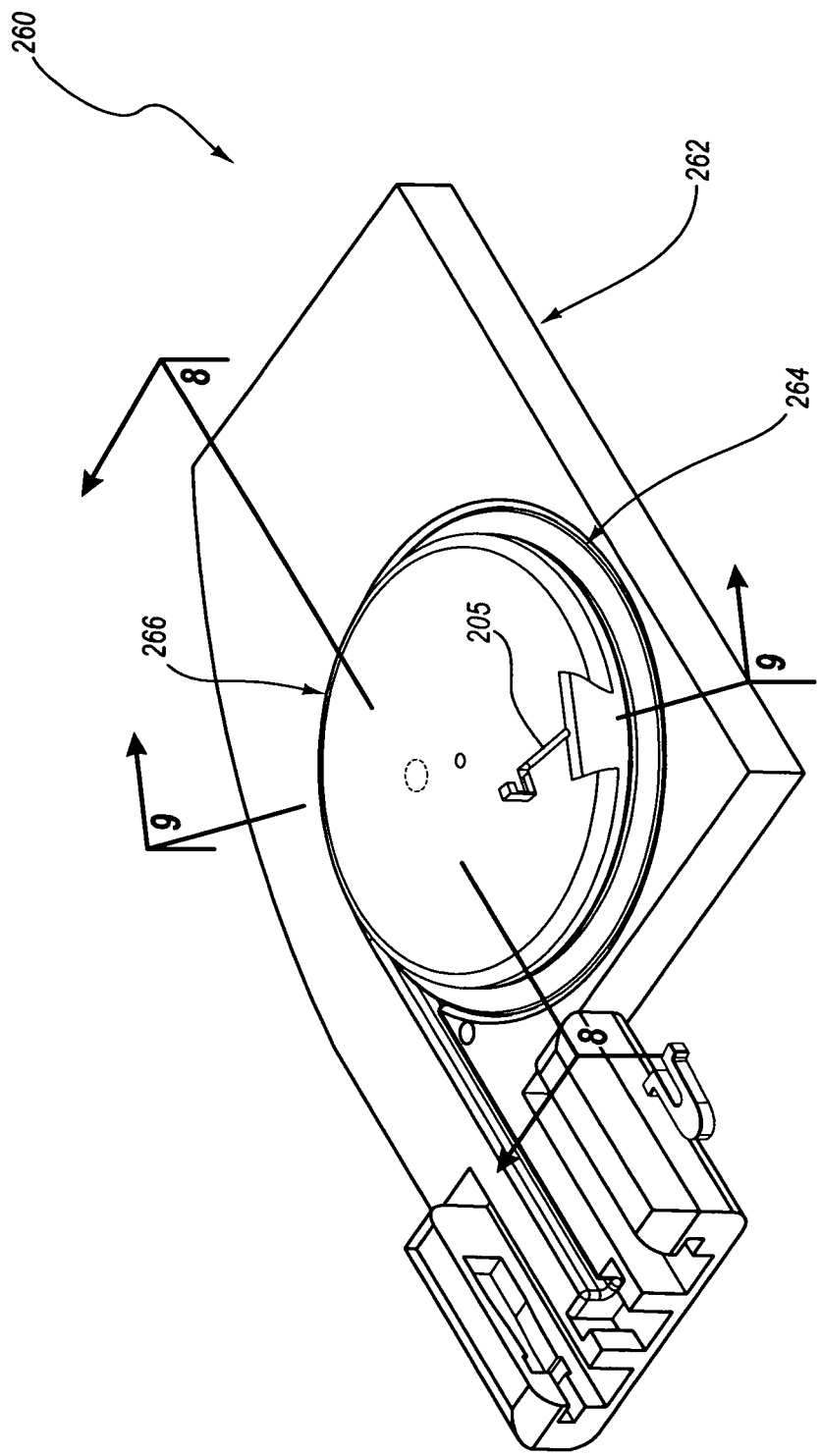
FIG. 7 is a perspective view of the automatic driving assembly of FIGS. 6A-B.
Figure 8:
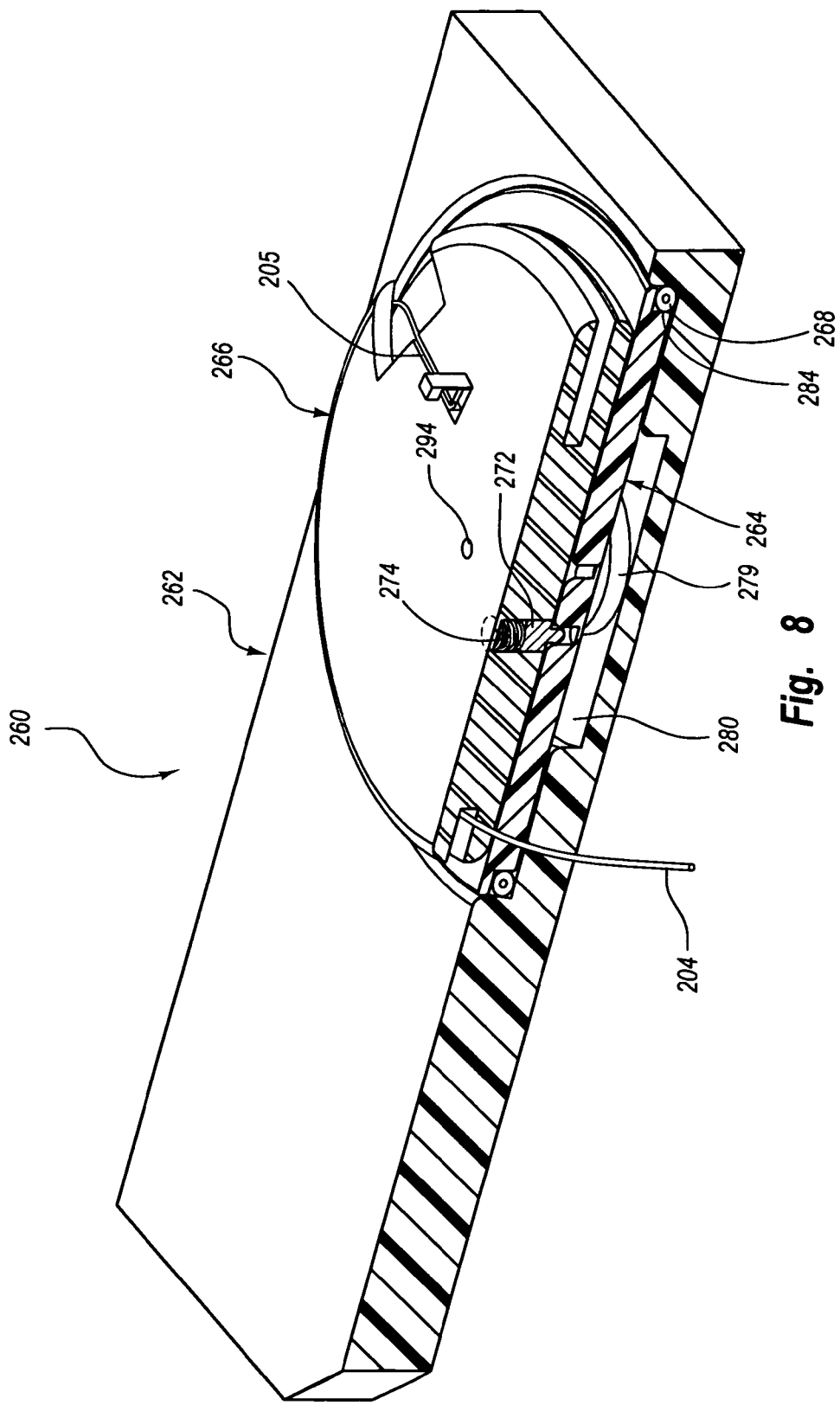
FIG. 8 is a cross-sectional view of the automatic driving assembly of FIG. 7 taken along cross-section indicators 8-8.
Figure 11:
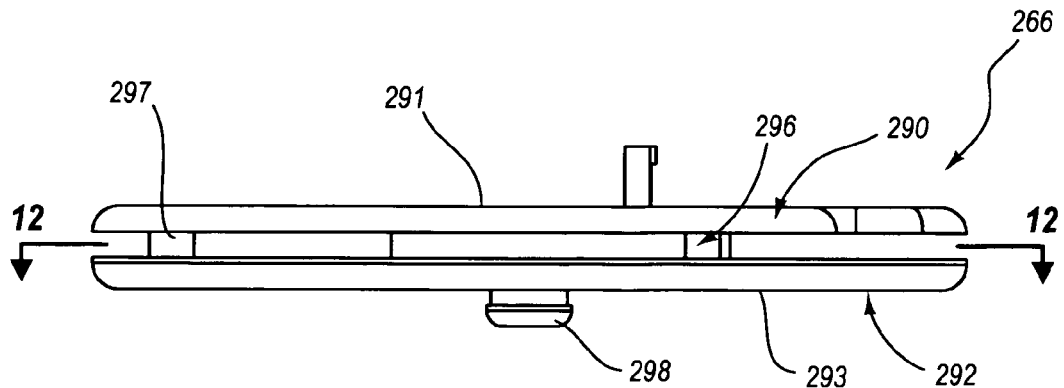
FIG. 11 is a side view of the spool assembly of the automatic driving assembly of FIG. 7.

The coil 268 includes a distal end 267 and a proximal end 269 (see FIG. 6). The distal end 267 may abut the compaction tube 212 (e.g., at a proximal end of the compaction tube 212). The proximal end 269 may abut the coil stop 285 of the driving plate 264. The cam shape of the cam surface 297 that the suture 204 follows as the spool assembly 266 rotates provides a variable linear force to the coil 268 through the driving plate 264 to advance the compaction tube 212 toward the sealing plug 210.

In some arrangements, the automatic driving assembly 260 may include the compaction tube 212. The compaction tube 212 and coil 268 may together define a compaction tube assembly. The compaction tube assembly may be positioned proximal of and adjacent to the sealing plug 210. The entire automatic driving assembly 260, including the compaction tube 212, may move together longitudinally within the housing 252 as shown by comparison of FIGS. 5C and 5E.

The automatic driving assembly 260 is located within the housing 252 at the proximal end portion 206 of the closure device 200. Embodiments of the automatic driving assembly 260 may be selectively disengagable. For example, operation of the release member 270, which protrudes through the release member aperture 281 in the housing 252, may release the spool assembly 266 to permit unspooling of the suture 204. Operating the release member 270 may release at least some length of the suture 204 from the housing 252. Unspooling or release of some length of the suture 204 after compaction of the sealing plug 210 permits the operator to withdraw the tissue puncture closure device 200 without further compacting the sealing plug 210. With the tissue puncture closure device 200 further withdrawn from the percutaneous incision 219, the operator is more easily able to cut the suture 204 at a location proximal of the sealing plug 210.

As shown in FIGS. 9-10, the driving plate 264 may be connected to the spool assembly 266. The suture 204 is connected to and at least partially wound about the spool assembly 266. The driving plate 264 tends to rotate at the same angular rate as the spool assembly 266 as a result of the connection between the driving plate 264 and spool assembly 266 with the spool connector 298.

Withdrawal of the closure device 200 from the tissue puncture 218 (if the anchor 208 is deployed and the automatic driving assembly 260 has contacted the stop in the housing 252 (see FIGS. 5E and 5G)) causes the suture 204 to unwind from the spool assembly 266. The spool assembly 266 rotates as the suture 204 unwinds and provides a torsional motive force that is transduced to a linear compaction force.

The torsional motive force provided by the spool assembly 266 is transduced into the linear compaction force by the driving plate 264, coil 268 and compaction tube 212. The driving plate 264 may be arranged coaxially with the spool assembly 266. When the spool assembly 266 rotates, it drives the driving plate 264, which in turn drives the coil 268. The coil 268 drives the compaction tube 212, which in turn compacts the sealing plug 210.

The compaction tube 212 is preferably tubular or semi-tubular and partially disposed about the suture 204 along its longitudinal axis. In some arrangements wherein the coil 268 also comprises the compaction tube 212, the coil 268 may comprise a semi-tubular shape having a generally U-shaped cross section, to provide a trough through which the suture 204 may enter and exit laterally. An open trough construction may permit the suture 204 and the coil 268 to merge as the spool assembly 266 unwinds. Accordingly, with the anchor 208 deployed, as the closure device 200 is retracted in a first, proximal direction, the suture 204 unwinds from the spool assembly 266, which drives the driving plate 264. The driving plate 264 drives the coil 268, and the coil 268 drives the compaction tube 212 in a second, opposite or distal direction. The compaction tube 212 compacts the sealing plug 210 toward the anchor 208.

Figure 5C:
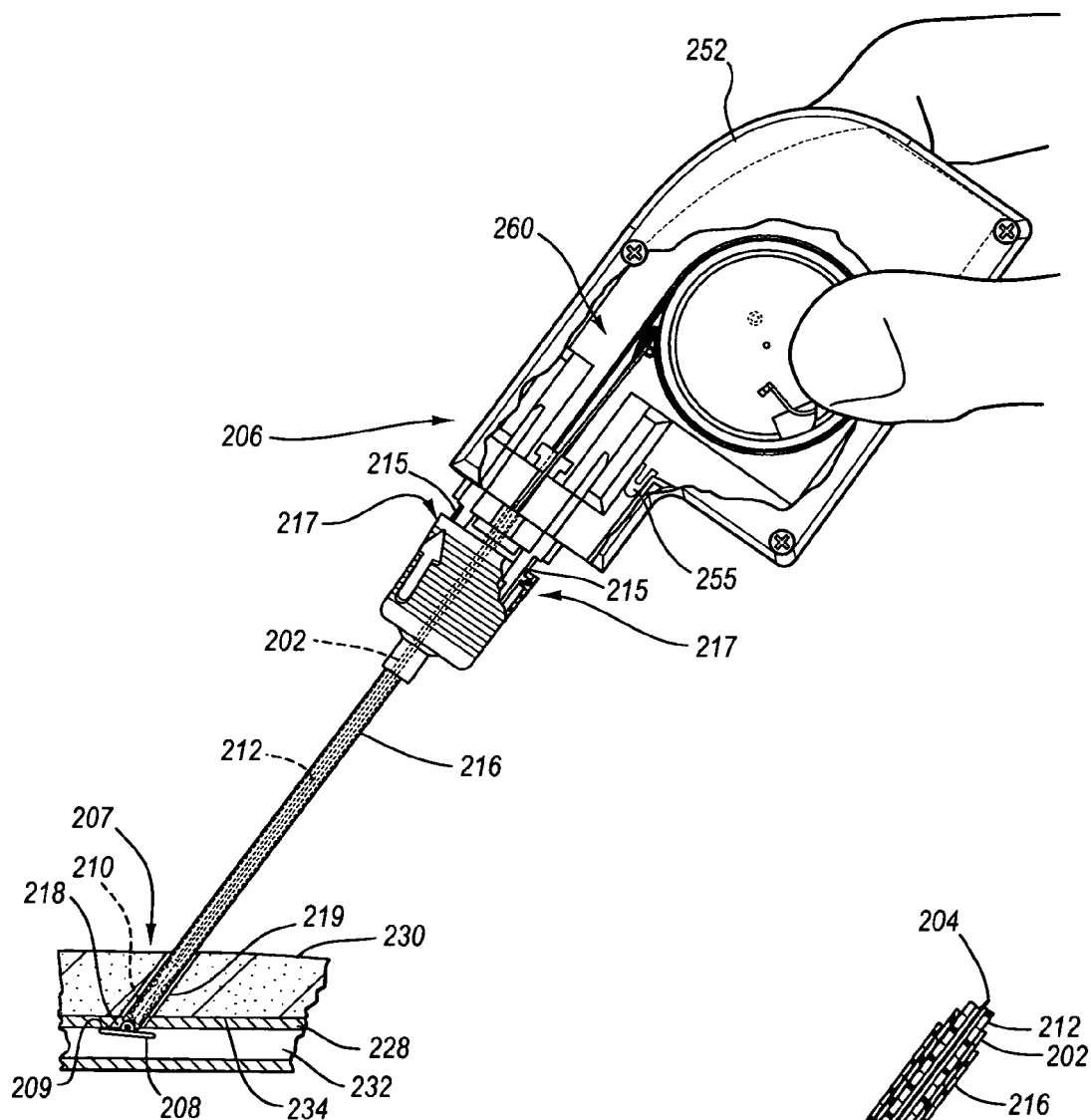
FIG. 5C is a side view of the tissue puncture closure device of FIG. 5A inserted through a procedure sheath and tissue puncture and engaged with a vessel in a first position.
Figure 5D:
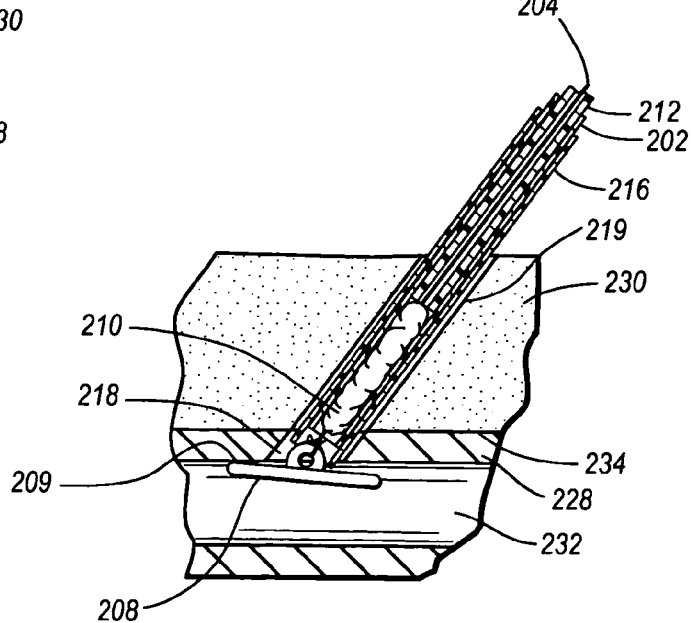
FIG. 5D is a detailed inset of FIG. 5C.
Figures 5E, 5F:
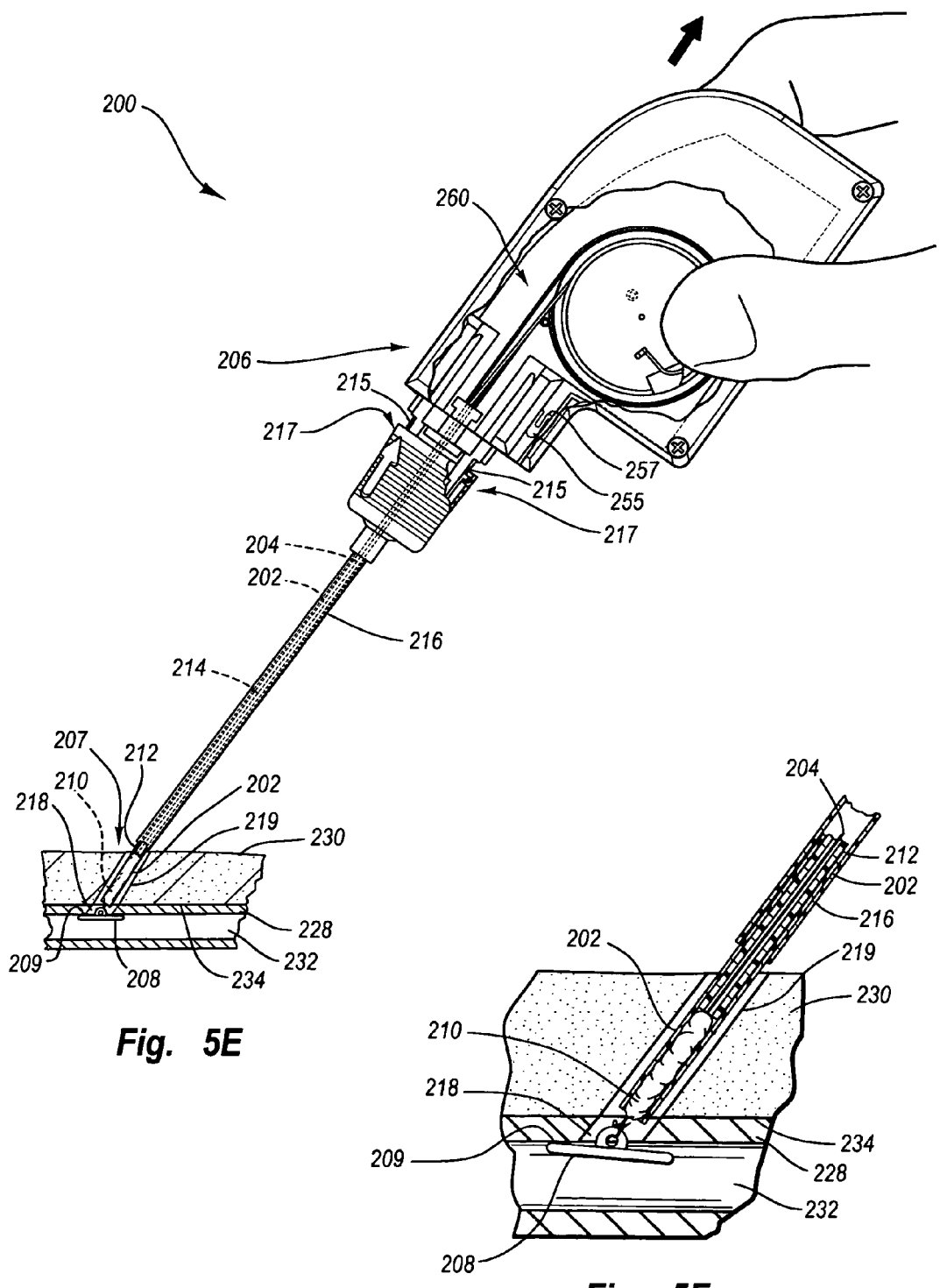
FIG. 5E is a side view of the tissue puncture closure device of FIG. 5A shown engaged with a vessel in a second position with the procedure sheath retracted.
FIG. 5F is a detailed inset of FIG. 5E.

In practice, the carrier tube 202 of the closure device 200 (containing the closure elements described above) is inserted into the procedure sheath 216, which is already inserted within the vessel 228 (see FIGS. 5C-5D). As the closure device 200 and the associated closure elements are inserted into the procedure sheath 216, the anchor 208 passes through and out of the distal end of the procedure sheath 216 and is inserted into the lumen 232. As mentioned above and shown in FIGS. 5A-5B, the anchor 208 is initially arranged substantially flush with the carrier tube 202 to facilitate insertion of the anchor 208 through the percutaneous incision 219 and into the lumen 232.

After the anchor 208 passes out of the distal end of the procedure sheath 216, the anchor 208 tends to deploy or rotate to the position shown in FIGS. 5C-5D. The closure device 200 may be partially withdrawn from the procedure sheath 216, catching the anchor 208 on the distal end of the procedure sheath 216 and rotating the anchor 208 to the position shown in FIGS. 5C-5D. The closure device 200 preferably includes a pair of biased fingers 215 that are lockingly received by a matching pair of recesses 217 in the procedure sheath 216. The locking arrangement between the biased fingers 215 and matching recesses 217 may fix the position of the housing 252 relative to the procedure sheath 216.

Following deployment of the anchor 208, the housing 252 and the procedure sheath 216 are withdrawn together. Withdrawing the housing 252 causes the anchor 208 to anchor itself within the vessel 228 against the vessel wall 234 as shown in FIGS. 5C-5D. Further withdrawing the housing 252 causes the automatic driving assembly 260 to slide forward in the housing 252 as shown in FIG. 5E-5F. Functionally, the anchor 208, sealing plug 210, carrier tube 202, procedure sheath 216, and automatic driving assembly 260 maintain the same axial position upon this further withdrawal of the housing 252, and the procedure sheath 216 and housing 252 move proximally (see FIGS. 5E-5F).

Referring to FIGS. 5E-5F, the distal end portion 207 of the carrier tube 202 is exposed within the percutaneous incision 219 as the housing 252 and the procedure sheath 216 are retracted. The carrier tube 202 may retain its position relative to the tissue puncture 218 until the housing 252 and the procedure sheath 216 have been retracted a predetermined distance. Relative movement between the housing 252/procedure sheath 216 and the carrier tube 202 may be facilitated by a sliding mount arrangement between the automatic driving assembly 260 and the housing 252. However, according to some embodiments the automatic driving assembly 260 is fixed to the housing 252.

As shown by the combination of FIGS. 5C-5H, the automatic driving assembly 260, which is attached to the carrier tube 202, may be free-floating or displaceable and slides relative to the housing 252 as the housing 252 and the procedure sheath 216 are retracted. However, the automatic driving assembly 260 may be initially held in a first position relative to the housing 252, as shown in FIG. 5C. For example, as shown in FIG. 5C, the tissue puncture closure device 200 may comprise a temporary holder such as a stowage detent 255 that releasably operates between the automatic driving assembly 260 and the housing 252. The stowage detent 255 may include a finger 257 with a protrusion to at least temporarily hold the automatic driving assembly 260 in the first position shown in FIG. 5C by contact with a webbing structure within the housing 252. In other arrangements, the stowage detent 255 may be mounted to the housing 252 and releasable contact the automatic driving assembly 260. The stowage detent 255 may be positioned at any desired location within the housing 252. For example, the stowage detent 255 may connected to a bottom surface of the automatic driving assembly 260 and be operably positioned within a slot formed in surface of the housing 252. Further, at least one slot and follower member may be positioned on the automatic driving assembly 260 and housing 252 to assist in maintaining relative axial movement between the automatic driving assembly 260 and housing 252 after release of the stowage detent.

Although the finger 257 tends to hold or temporarily lock the automatic driving assembly 260 in the first position shown in FIG. 5C, the finger 257 releases when a sufficient predetermined force is applied between the housing 252 and the automatic driving assembly 260. For example, with the anchor 208 deployed, a retraction force provided by a user to the housing 252 causes the finger 257 to deflect inward and release. Thereafter, the finger 257 provides little resistance to sliding movement between the automatic driving assembly 260 and the housing 252. Accordingly, retraction of the housing 252 may retract the procedure sheath 216, which is fixedly connected to the housing 252, but the automatic driving assembly 260 and the carrier tube 202 may slide relative to the housing 252 and therefore remain in position with respect to the tissue puncture 218 (see FIG. 5E). The automatic driving assembly 260 may slide a predetermined distance with respect to the housing 252 until the automatic driving assembly 260 reaches a stop (e.g., a distal internal wall of the housing 252). The predetermined distance may be at least long enough to expose the slit 209 (see FIG. 5A) in the carrier tube 202 to facilitate later removal of the sealing plug 210 from the carrier tube 202.

Figures 5G, 5H:
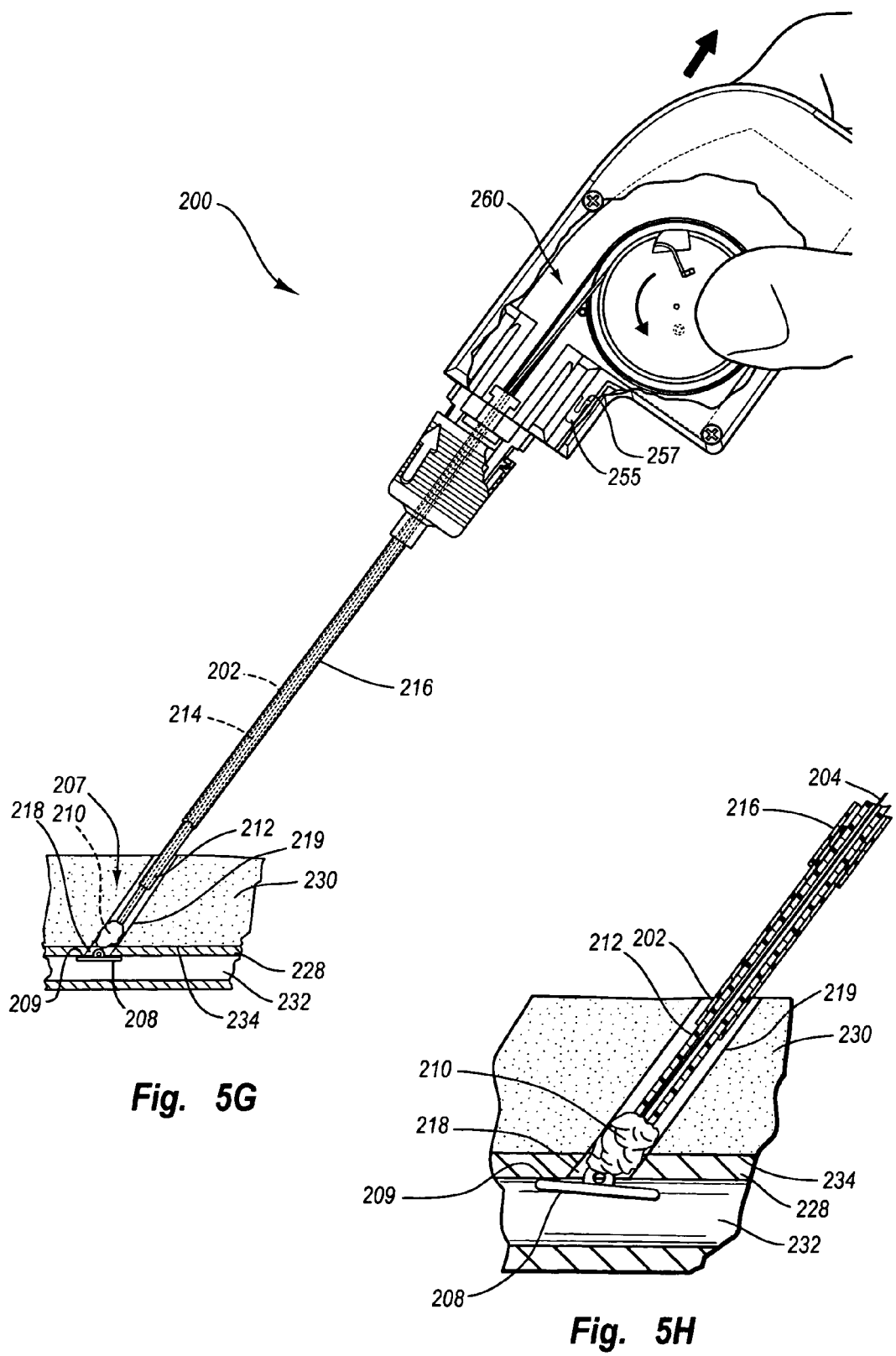
FIG. 5G is a side view of the tissue puncture closure device of FIG. 5A engaged with a vessel in a third fourth position with a carrier tube retracted to expose a sealing plug adjacent to the tissue puncture and the sealing plug being compacted.
FIG. 5H is a detailed inset of FIG. 5G.

When the automatic driving assembly 260 reaches the stop, further retraction of the housing 252 withdraws the carrier tube 202 as well, ejecting the sealing plug 210 automatically. The spool assembly 266 begins to rotate to permit unwinding of some of the suture 204 from the spool. Typically, the driving plate 264, which rotates with the spool assembly 266, unwinds an amount to advance the coil 268 and compaction tube 212 and compact the sealing plug 210, as shown in FIGS. 5G-5H. Still further retraction of the housing 252 further rotates the spool assembly 266 and driving plate 264 to advance the coil 268 and compaction tube to complete compaction of the sealing plug 210.

Any further retraction of the housing 252 exceeds a threshold torsional force between the driving plate 264 and spool assembly 266 that causes the follower 272 to move out of the follower recess 288 of the driving plate 264. The driving plate 264 and spool assembly 266 are then able to rotate relative to each other without further compacting the sealing plug 210. The interaction between the follower 272 and follower recesses 288 provides a clutch function. The follower 272 and follower recesses 288 may be referred to as a clutch or clutch assembly of the automatic driving assembly.

Upon completion of compacting the sealing plug 210, the operator may actuate the release member 270 to permit unwinding of the suture 204 from the spool assembly 266. The suture 204 may then be better exposed for cutting near the tissue layer 230 to release the housing 252 from the anchor 208/sealing plug 210.

Unlike previous closure devices that require a separate, manual compaction procedure following the deposition of the sealing plug 210, the closure device 200 of the present disclosure automatically compacts the sealing plug 210 by applying a retracting force to the housing 252. The sealing plug 210 may be compacted during or after withdrawal of the carrier tube 202, reducing or eliminating any gaps that may otherwise occur between the sealing plug 210 and the tissue puncture 218 in the vessel 228.

In addition, by placing tension on or pulling the suture 204 away from the percutaneous incision 219, the suture 204 may cinch and lock (with a slip-knot or the like) together the anchor 208 and the sealing plug 210, sandwiching the vessel wall 234 between the anchor 208 and sealing plug 210. The force exerted by the compaction tube 212 and the cinching together of the anchor 208 and sealing plug 210 by the suture 204 also causes the sealing plug 210 to deform radially outward within the percutaneous incision 219 and function as an anchor on the proximal side of the tissue puncture 218 as shown in FIGS. 5G-5H.

Many variations are possible for the features of tissue puncture closure device 200. In some arrangements, the coil 268 may be permanently connected to the driving plate 264. The driving plate 264 may be directly connected to the compaction tube 212. Generally, any device or construction that uses a disengagable cam structure driven by rotation of a spool member (about which the suture is wound) to advance a compaction member to compact a sealing plug falls within the spirit and scope of the present disclosure.

Operation of the embodiment of FIGS. 5A-5H is as follows. As the housing 252 of the closing device 200 is retracted from the percutaneous incision 219, as shown in FIG. 5C, the stowage detent 255 releases. The automatic driving assembly 260 and carrier tube 202 may remain stationary and therefore float relative to the housing 252. The procedure sheath 216 is retracted as the housing 252 is withdrawn, exposing the distal end portion 207 of the carrier tube 202. The automatic driving assembly 260 eventually contacts a stop (or, in some embodiments, the automatic driving assembly is fixed), and further retraction causes the automatic driving assembly 260 and carrier tube 202 to retract as well. As the automatic driving assembly 260 retracts, the suture 204, which is threaded through the anchor 208, unwinds from the spool assembly along a cam suture path and causes rotation of the spool assembly 266 and driving plate 264 with a variable rotation force.

As the driving plate 264 rotates, the coil 268 is advanced to drive and advance the compaction tube 212. In some arrangements, the coil 268 may be long enough and constructed such that the coil 268 functions as the compaction tube 212. The compaction tube 212 compacts the sealing plug 210. Therefore, as the closing device 200 is retracted from the percutaneous incision 219, the procedure sheath 216 may be retracted (see FIGS. 5E-5F), the carrier tube 202 may be retracted, and the sealing plug 210 is automatically compacted (see FIGS. 5G-5H). The sealing plug 210 is more likely to create a sufficient arterial seal without a gap relative to the anchor 208, as may otherwise occur with a separate manual compaction procedure.

Compaction of the sealing plug 210 may be confirmed by further retraction of the housing 252 until the follower 272 moves out of the follower recesses 288 to permit relative rotation between the driving plate 264 and spool assembly 266 (also referred to as a clutch operation of the automatic driving assembly 260). This relative rotation may be signaled to the operator of the tissue puncture closure device 200 with a tactile or audible "click" or other indicator. The clutch action between the driving plate 264 and spool assembly 266 may limit the possibility of over compaction of the sealing plug 210 into the vessel 228.

When the sealing plug 210 has been sufficiently compacted, the automatic driving assembly 260 may be disengaged, enabling further retraction of the closure device 200 without additional compaction. The automatic driving assembly 260 may be advantageously disabled by activating the release member 270 out of contact with the driving plate 264. Activating the release member 270 allows the suture 204 to at least partially unwind from the spool assembly 266 without driving the compaction tube 212. Unwinding the spool assembly 266 exposes a sufficient length of the suture 204 distal of the compaction tube 212 to allow an operator to cut the suture 204 and separate the sealing plug 210 and anchor 208 from the remainder of the closure device 200.

Figure 13:
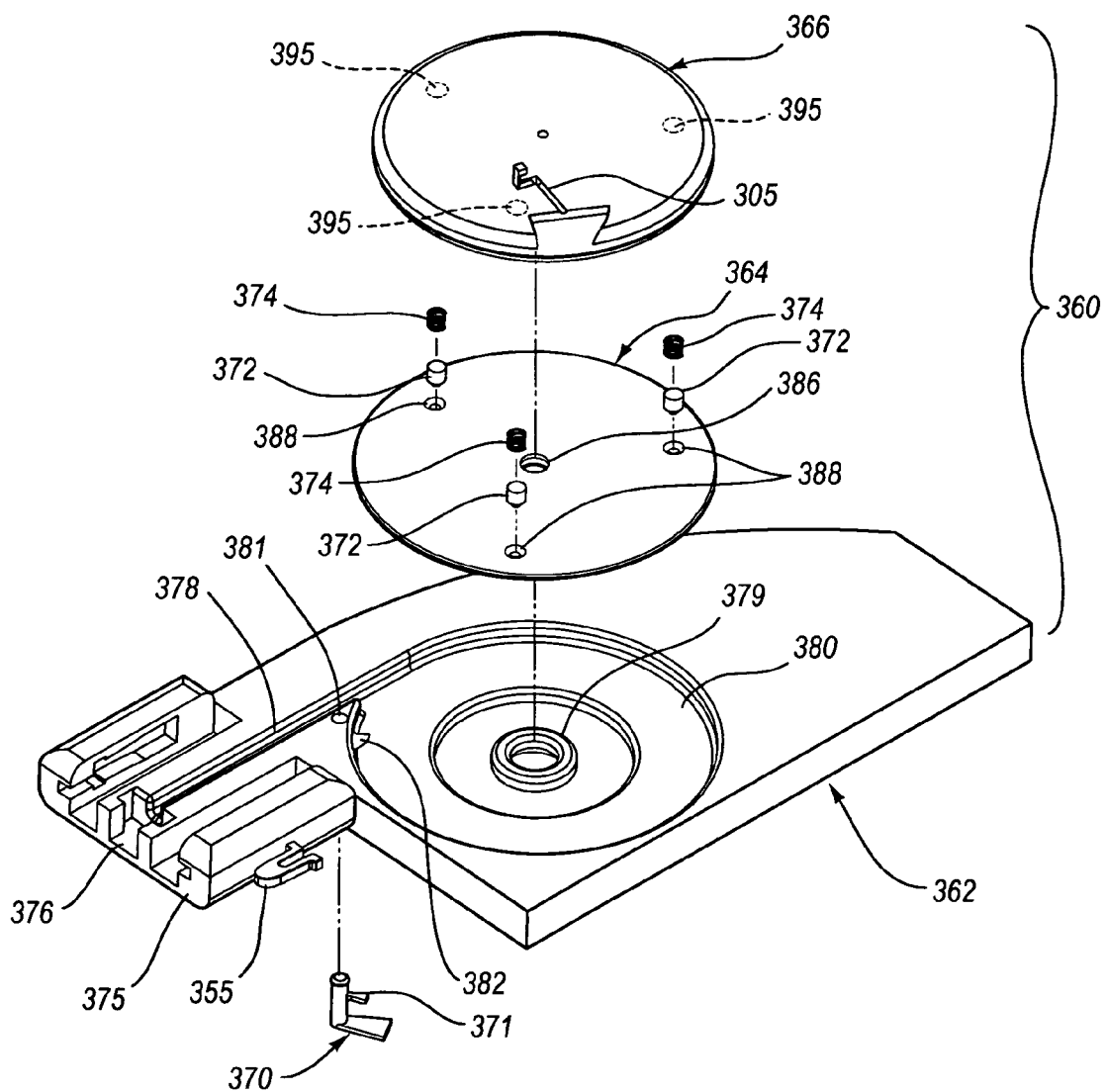
FIG. 13 is an exploded perspective view of another example tissue puncture closure device with an automatic compaction or driving mechanism according to the present disclosure.

In an alternative construction shown in FIG. 13, an automatic driving assembly 360 includes a plurality of followers 372 carried by a spool assembly 366 that interface with a plurality of follower recesses 388 defined in a driving plate 364. The automatic driving assembly 360 includes a base 362 having a distal end 375, a connector recess 376, a coil recess 378, a mounting hub 379, a spool recess 380, and first and second release member apertures 381, 382. The operation and function of the base 362 may be the same or similar to the base 262 described herein. The driving plate 364 may a connector aperture 386, a plurality of follower recesses 388, and other features that are the same or similar with the same or similar function as the driving plate 264 described herein. The spool assembly 366 may include a plurality of follower cavities 395 receptive of the plurality of followers 372 and biasing members 374 at positions offset from the center of the spool assembly 366. The spool assembly 366 may include other features that are the same or similar with the same or similar function as the spool assembly 266 described herein.

The use of a plurality of followers 372 that operate independently to move into and out of corresponding follower recesses 388 of the driving plate 364 may provide certain advantages. For example, but without limitation, the use of multiple followers 372 may provide improved consistency in the threshold level of torsional force required to move the followers 372 out of the follower recesses 388 to permit relative rotation between the driving plate 364 and spool assembly 366. Further, the use of multiple followers 372 may provide improved safety and assurance of operability during use. The use of multiple followers 372 and/or multiple follower recesses 388 may provide additional precision and control of the amount of free rotation of the spool assembly 366 relative to the driving plate 364 after one or more of the followers 372 move out of one or more of the follower recesses 388.

The preceding description has been presented only to illustrate and describe exemplary embodiments of the present disclosure. It is not intended to be exhaustive or to limit the invention to any precise form disclosed. Many modifications and variations are possible in light of the above teaching. It is intended that the scope of the invention be defined by the following claims.

What is claimed is:

1. A tissue puncture closure device, comprising:
   an anchor;
   a sealing plug;
   a filament secured between the sealing plug and the anchor;
   a compaction member assembly disposed adjacent the sealing plug and structured and arranged to apply an axially directed compressive force to automatically compact the sealing plug toward the anchor, the compaction member assembly having a distal end and a proximal end;
   a spool having a portion of the filament wound thereon, the spool having a center;
   a follower cavity defined in the spool at a position offset from the center of the spool;
   a driving plate connected to the spool and arranged to contact and apply a force to the proximal end of the compaction member assembly upon rotation of the driving plate to advance the compaction member assembly;
   a follower carried by the follower cavity of the spool, the follower operable between the spool and driving plate to releasably connect the spool and driving plate.

2. A tissue puncture closure device according to claim 1 wherein the compaction member assembly includes a compaction tube and a coil, the coil being structured and arranged to apply an axially directed compressive force to the compaction tube to drive the compaction tube to automatically compact the sealing plug toward the anchor.

3. A tissue puncture closure device according to claim 2 wherein the compaction member assembly includes a compaction tube and a coil member arranged end-to-end, the compaction tube defining the distal end of the compaction member assembly and the coil defined the proximal end of the compaction member assembly.

4. A tissue puncture closure device according to claim 1 wherein the spool includes a cam portion, a portion of the filament being wrapped around the cam portion, wherein unwinding the filament from the spool applies a variable rotation force to the driving plate.

5. A tissue puncture closure device according to claim 1 wherein the spool includes first and second outer plates and a cam portion positioned between the first and second outer plates, the cam portion defining a cam surface having a variable radius, wherein a portion of the filament wraps around the cam portion.

6. A tissue puncture closure device according to claim 1 wherein the follower is mounted to the spool and is biased toward the driving plate.

7. A tissue puncture closure device according to claim 6 wherein the driving plate includes at least one recess sized to receive a portion of the follower.

8. A tissue puncture closure device according to claim 1 wherein the driving plate includes a coil track defined in a peripheral surface of the driving plate, a portion of the compaction member assembly being positioned in the coil track.

9. A tissue puncture closure device for partial insertion into and sealing of a tissue puncture in an internal tissue wall accessible through a percutaneous incision, comprising:
   an anchor for disposition on a distal side of the internal tissue wall;
   a sealing plug for disposition on a proximal side of the internal tissue wall;

a filament connected to and anchored at a distal end to the anchor and sealing plug, the sealing plug being slidable and cinchable along the filament toward the anchor to close the tissue puncture;

a compaction member assembly disposed on the filament and arranged to drive the sealing plug along the filament distally towards the anchor;

a storage spool onto which a proximal end of the filament is wound;

a follower cavity formed in the storage spool;

a driving plate connected to the storage spool, the driving plate configured to contact a proximal end of the compaction member assembly to advance the compaction member assembly;

at least one follower mounted to the storage spool in the follower cavity, the at least one follower biased into contact with the driving plate to releasably resist relative rotational movement between the storage spool and the driving plate.

10. A tissue puncture closure device of claim 9 wherein the driving plate includes at least one recess configured to receive a portion of the at least one follower.

11. A tissue puncture closure device of claim 10 wherein the at least one recess includes a plurality of recesses arranged in a circle.

12. A tissue puncture closure device of claim 10 wherein the at least one follower moves out of the at least one recess when a threshold torsional force applied to the storage spool by the filament is exceeded.

13. A tissue puncture closure device of claim 9 wherein the storage spool includes a cam portion about which the proximal end of the filament is wound, the storage spool being configured to apply a variable rotational force to the driving plate when the filament unwinds from the cam portion.

14. A method of sealing a tissue puncture in an internal tissue wall of a vessel accessible through a percutaneous incision, the method comprising: providing a closure device having an anchor, a sealing plug, a filament secured between the sealing plug and the anchor, a compaction member assembly disposed adjacent the sealing plug and structured and arranged to apply an axially directed compressive force to automatically compact the sealing plug toward the anchor, the compaction member assembly having a distal end and a proximal end, a spool having a center and a portion of the filament wound thereon, a follower cavity defined in the spool at a position offset from the center of the spool, a driving plate connected to the spool and arranged to contact and apply a force to the proximal end of the compaction member assembly upon rotation of the driving plate to advance the compaction member assembly, and at least one follower carried by the follower cavity of the spool and arranged to resist relative rotational movement between the driving plate and spool, the distal end of the compaction member assembly being disposed adjacent the sealing plug, the proximal end of the compaction member assembly being in contact with the driving plate, and the driving plate being connected to the spool; inserting the anchor through the tissue puncture; withdrawing the closure device from the tissue puncture with the anchor positioned within the vessel, wherein withdrawing the closure device rotates the spool, and rotating the spool rotates the driving plate to drive the compaction member assembly and compact the sealing plug toward the anchor; further withdrawing the closure device until the at least one follower disconnects from at least one of the spool and driving plate to permit relative rotation between the spool and driving plate.

15. A method according to claim 14 wherein the at least one follower is mounted to the spool and is biased into contact with the driving plate with a biasing member.

16. A method according to claim 14 wherein the at least one follower includes a plurality of followers biased into contact with the driving plate.

17. A method of sealing a tissue puncture in an internal tissue wall accessible through a percutaneous incision, comprising: providing a tissue puncture closure device comprising an anchor, a sealing plug, a filament secured between the sealing plug and the anchor, a compaction member assembly disposed adjacent the sealing plug and structured and arranged to apply an axially directed compressive force to automatically compact the sealing plug toward the anchor, the compaction member assembly having a distal end and a proximal end, a driving plate connected to the spool and arranged to contact and apply a force to the proximal end of the compaction member assembly upon rotation of the driving plate to advance the compaction member assembly, a spool having a cam member and a center and having a portion of the filament would thereon, and at least one follower carried by a follower cavity defined in the spool at a position offset from the center of the spool, the filament having a distal end connected to the anchor, to the sealing plug located proximal of the anchor, and to the cam member of the spool at a proximal end of the filament, the at least one follower being operable to releasably connect the spool and driving plate; inserting the tissue puncture closure device into the percutaneous incision; deploying the anchor into the tissue puncture; automatically compacting the sealing plug toward the anchor upon withdrawal of the tissue puncture closure device from the tissue puncture, wherein automatically compacting includes unwinding the filament from the spool to rotate the spool and driving plate together to apply a variable force to the compaction member assembly to advance a distal end of the compaction member assembly; operating the at least one follower to release the spool from rotating with the driving plate; cutting the filament to leave the anchor and sealing plug at the tissue puncture.

18. A method according to claim 17 wherein operating the at least one follower includes applying a withdrawal force to the tissue puncture closure device to exceed a threshold torsional force applied to the spool by unwinding in the filament to automatically move the at least one follower relative to at least one of the spool and driving plate.

19. A method according to claim 17 wherein the driving plate includes a plurality of follower recesses arranged to receive the at least one follower at different relative rotated positions between the driving plate and spool.

20. A method according to claim 17 wherein the tissue puncture closure device includes a housing and a base upon which the driving plate and spool are mounted, the base being movable within the housing to permit ejection of the sealing plug from the tissue puncture closure device without compacting the sealing plug.

21. A tissue puncture closure device, comprising:

an anchor;

a sealing plug;

a filament secured between the sealing plug and the anchor;

a compaction member assembly disposed adjacent the sealing plug and structured and arranged to apply an axially directed compressive force to automatically compact the sealing plug toward the anchor, the compaction member assembly having a distal end and a proximal end;

a spool having a portion of the filament wound thereon, the spool including first and second outer plates and a cam portion positioned between the first and second outer plates, the cam portion defining a cam surface having a variable radius, wherein a portion of the filament wraps around the cam portion;

a driving plate connected to the spool and arranged to contact and apply a force to the proximal end of the compaction member assembly upon rotation of the driving plate to advance the compaction member assembly;

a follower operable between the spool and driving plate to releasably connect the spool and driving plate.

22. A tissue puncture closure device, comprising:

an anchor;

a sealing plug;

a filament secured between the sealing plug and the anchor;

a compaction member assembly disposed adjacent the sealing plug and structured and arranged to apply an axially directed compressive force to automatically compact the sealing plug toward the anchor, the compaction member assembly having a distal end and a proximal end;

a spool having a portion of the filament wound thereon;

a follower cavity defined in the spool;

a driving plate connected to the spool and arranged to contact and apply a force to the proximal end of the compaction member assembly upon rotation of the driving plate to advance the compaction member assembly;

a follower carried by the follower cavity of the spool, the follower operable between the spool and driving plate to releasably connect the spool and driving plate, wherein the follower is mounted to the spool and is biased toward the driving plate.

23. The tissue puncture closure device according to claim 22, wherein the driving plate includes at least one recess sized to receive a portion of the follower.

* * * * *